United States Patent [19]
Hsia

[11] Patent Number: 6,006,762
[45] Date of Patent: Dec. 28, 1999

[54] DENTAL FLOSS APPLICATOR

[76] Inventor: Chih-Yu Hsia, 301 Warren Way, Arcadia, Calif. 91007

[21] Appl. No.: 09/225,383

[22] Filed: Jan. 4, 1999

[51] Int. Cl.$^6$ ..................................................... A61C 15/00
[52] U.S. Cl. ........................... 132/327; 132/325; 132/323
[58] Field of Search ................................... 132/322, 323, 132/324, 325, 326, 327, 328, 329

[56] References Cited

U.S. PATENT DOCUMENTS

| | | | |
|---|---|---|---|
| 3,913,597 | 10/1975 | Day | 132/323 |
| 4,022,229 | 5/1977 | Minka | 132/323 |
| 4,031,909 | 6/1977 | Kelley | 132/323 |
| 4,206,774 | 6/1980 | Griparis | 132/323 |
| 4,495,956 | 1/1985 | Fourie | 132/323 |
| 4,522,216 | 6/1985 | Bunker . | |
| 4,817,642 | 4/1989 | Lipp | 132/324 |
| 4,936,326 | 6/1990 | Eckroat | 132/326 |
| 5,261,430 | 11/1993 | Mochel | 132/322 |
| 5,327,977 | 7/1994 | Lukashuk | 132/324 |
| 5,762,078 | 6/1998 | Zebuhr | 132/322 |

*Primary Examiner*—Gene Mancene
*Assistant Examiner*—Pedro Philogene
*Attorney, Agent, or Firm*—William W. Haefliger

[57] ABSTRACT

A dental floss applicator includes an applicator head, and protrusions on the head defining first and second floss engaging surfaces, and a third surface spaced from the first and second surfaces, to engage a primary strand of floss extending from the first surface to the third surface, and to engage a secondary strand of floss extending from the second surface to the third surface. The strands may be portions of a continuous loop of floss engaging all three surfaces, which may be located on multiple legs protruding from the head, and that loop may be disengagable from the one leg for finger simultaneous manipulation of two spaced flossing strands as during flossing.

18 Claims, 32 Drawing Sheets

DENTAL FLOSS APPLICATOR

BACKGROUND OF THE INVENTION
1. Field of the Invention

This invention relates to improved dental floss application methods and applicators and particularly to devices that allow a user to easily use dental floss to clean teeth.
2. Descriptions of the Prior Arts Various dental floss applicators have been indicated in the prior arts such as U.S. Pat. Nos. 3,759,272; 3,814,114; 3,850,182; 3,871,393; 3,915,178; 4,522,216; 4,691,719; 4,706,694; 4,790,336; 4,995,361; 5,020,554; 5,094,256; 5,113,880; 5,141,008; 5,170,809; 5,176,157; 5,183,064; 5,280,797; 5,375,614; 5,375,615; 5,433,227; 5,450,866; 5,469,874; 5,483,982; 5,579,786; and 5,606,984. Except for U.S. Pat. No. 4,522,216, each of these referenced prior arts indicates a device that provides a single dental floss line that can be inserted between two teeth for dental cleaning. The U.S. Pat. No. 4,522,216 does not address mean to readily provide new floss strands for flossing. The present invented devices and methods provide two dental floss lines that form a partial loop around a tooth for cleaning purposes. The present invented devices provide mean to supply new floss strand for flossing.

SUMMARY OF THE INVENTION

Six kinds of the invented devices and their combinations are introduced.

Basically, each of them consists of:
a) a handle mean;
b) an optional connection mean;
c) and an applicator head mean.

The invented devices will provide a semi loop of a dental floss which can be inserted between a tooth. The semi loop of the dental floss can be used as a scraper to move up and down along three sides of a tooth to clean the tooth. The invented devices will also allow a user to replace a used dental floss with a new one.

These and other objects and advantages of the invention, as well as the details of an illustrative embodiments, will be more fully understood from the following specification and drawings, in which:

DRAWING DESCRIPTION

The invention is illustrated by reference to the accompanying drawings, in which:

FIG. 19 shows that a line of dental floss is attached onto the invented device for use.

FIG. 22 shows that a line of dental floss is attached onto the invented device for use.

GENERAL DESCRIPTION

Figure 1:
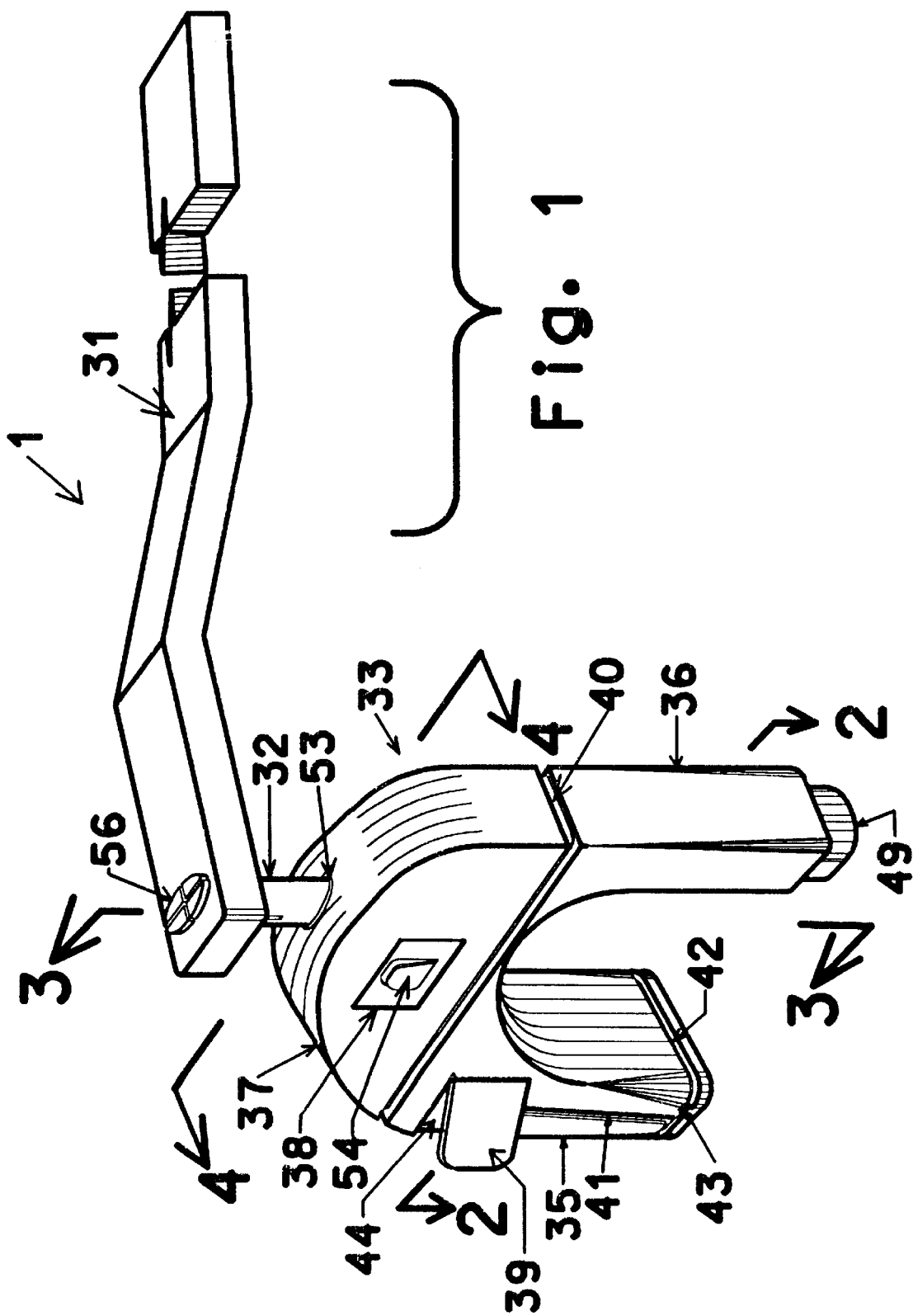
FIG. 1 is a perspective view of the first variation of the invented device.
Figure 2:
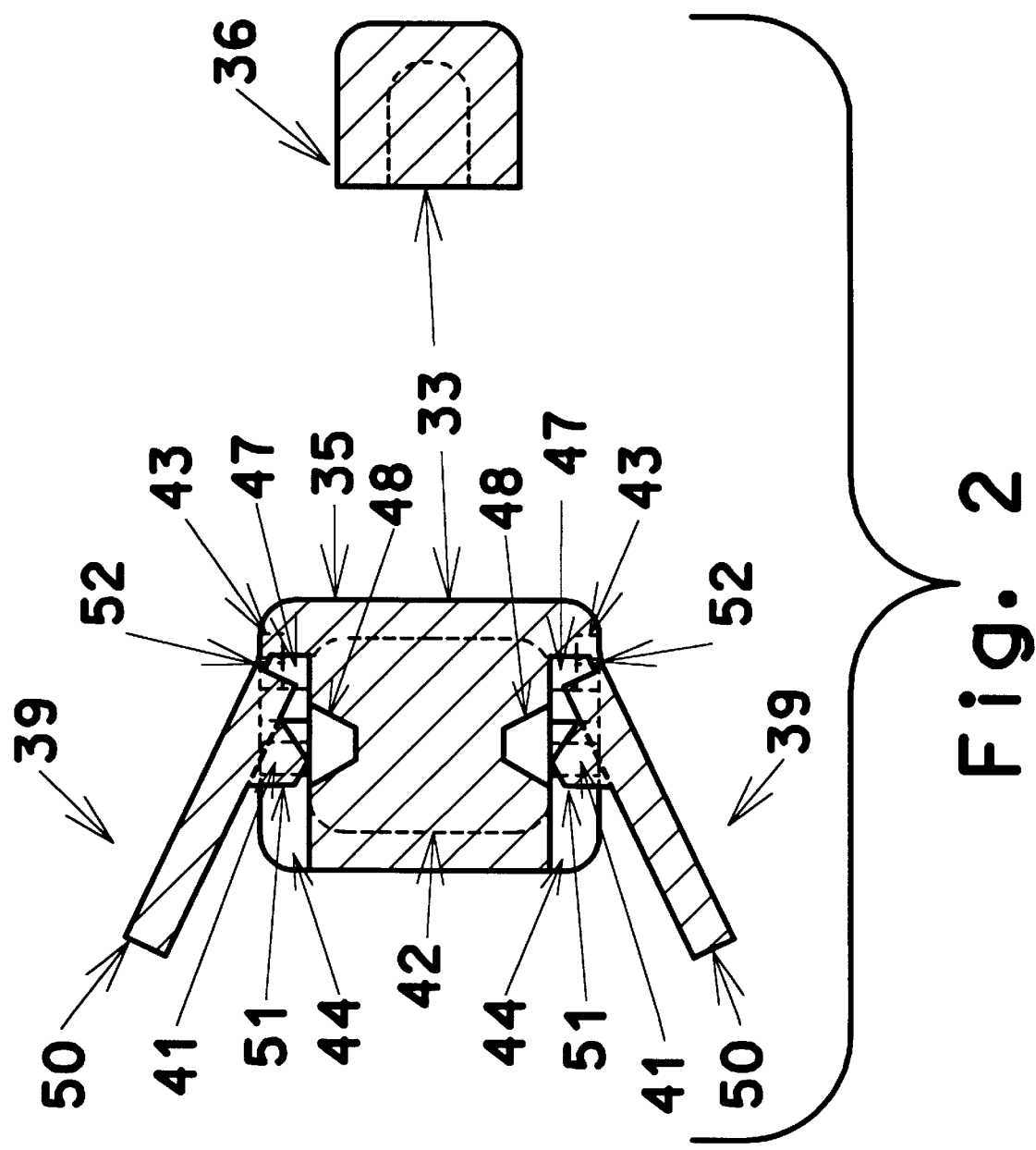
FIG. 2 is a sectional view of the device shown in FIG. 1.

Six variations of the invented device are introduced herein in this specification.

Referring to FIGS. 1 through 4, the first variation of the invented dental floss applicator 1 consists of a handle 31, a connector 32, and an applicator head 33.

The handle is an elongated object that can be held comfortably by a hand. A hole 34 is located near one end of the handle.

The applicator head consists of a wide leg 35, a narrow leg 36, a base 37, one or two cutters 38, two lockers 39, a floss holder 40, and one or two floss guide 41. The wide leg, the narrow leg and the base form a "U"-shaped object that basically the applicator head is.

The wide leg 35 is the wider leg of the "U"-shaped applicator head while the narrow leg 36 is the narrower one. The wide leg is a leg which has a floss groove 42 near its bottom, a pair of floss guard 43 in the floss groove, and a pair of recessed area 44 near its top where the wide leg joins with the base 37. The floss groove is a groove that is around the bottom rim of the wide leg. The floss guards are on two opposite exterior sides of the wide leg. The floss guard consists of two plates, the upper plate 45 and the lower plate 46. The upper plate is a plate that extrudes from the top rim of the floss groove to more than half of the width of the floss groove. The lower plate is a plate that extrudes from the bottom rim of the floss groove to more than half of the width of the floss groove. The edges of the upper plate and the lower plate are offset so that a gap exists between the edges of the two plates. There is a space 47 in the floss groove between the floss guard and the end wall of the floss groove. The recessed area 44 is a recessed area on the wide leg. A keyhole 48 is a depressed area on the recessed area.

The narrow leg 36 is a leg with an extruding block 49 at one end. The other end of the narrow leg joins the base of the applicator head. The extruding block is a block that extrudes from the end of the narrow leg. The extruding block has a cross-sectional area that is smaller than this of the narrow leg.

The locker 39 consists of a plate 50, a key 51, and a flexible hinge 52. The plate 50 is a plate. The plate is slightly narrower than the recessed area 44 so that the plate can fit in and engage with the edges of the recessed area. The plate is longer than the recessed area therefore on edge of the plate extrudes outside of the recessed area. The flexible hinge 52 is a thinned portion of the plate. The flexible hinge connects the plate and the wide leg. The key 51 is an object that extrudes from the surface of the plate. The key can be fitted into and engage with the keyhole 48 of the recessed area.

The base 37 is the arm of the "U"-shaped applicator head. A hole 53 penetrates the base near its center. The hole is in a direction generally parallel to the two legs of the applicator head. The floss holder 40 is a groove around the base's lower portion near where the two legs begin. The cutter 38 is a plate with a partially punched-out plate 54 which has sharp edges which can serve as knifes. The cutter is mounted on a side wall of the base. The floss guide 41 is also a groove on the surfaces of the wide leg. The floss guide runs from the floss groove 42 to the recessed area 44.

The connector 32 is a rod with split enlarged ends 56 and with hollow centers 57 near both ends. On end of the connector penetrates and engages with the hole 34 of the handle. The other end of the connector penetrates and engages with the hole 53 of the base of the applicator head. The applicator head can rotate around the axis of the connector.

Figure 3:
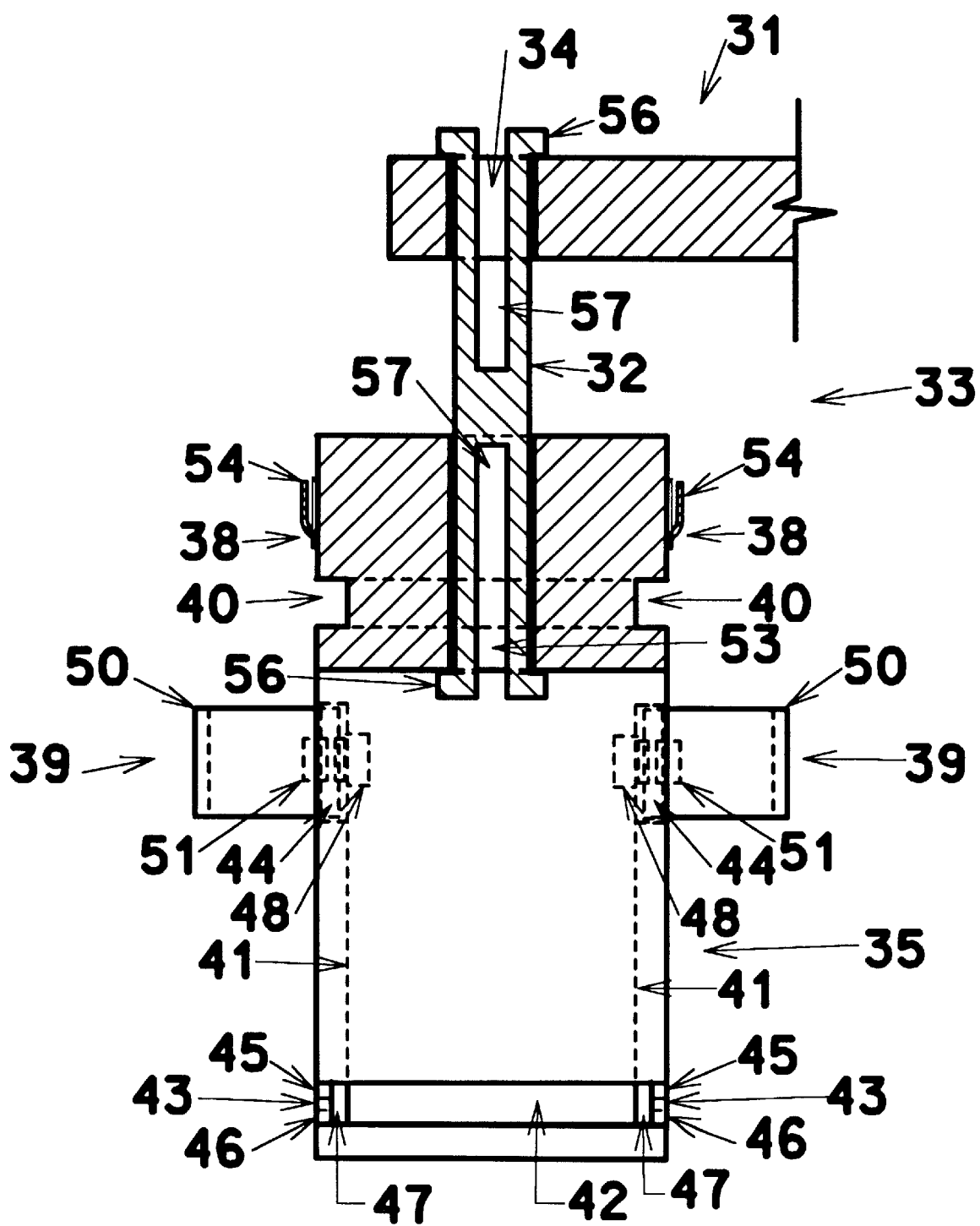
FIG. 3 is an another sectional view of the device shown in FIG. 1.
Figure 4:
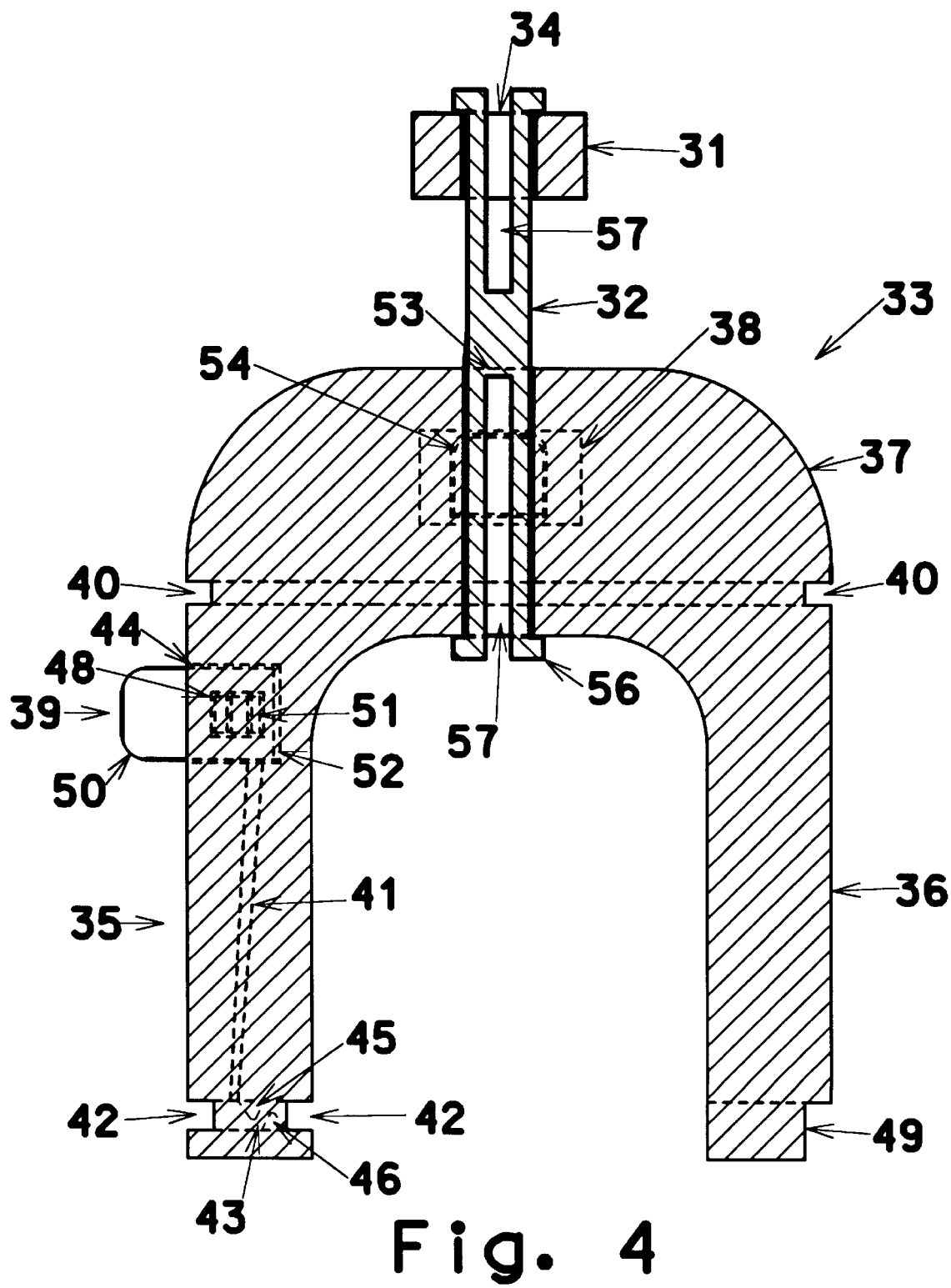
FIG. 4 is an another sectional view of the device shown in FIG. 1.
Figure 5:
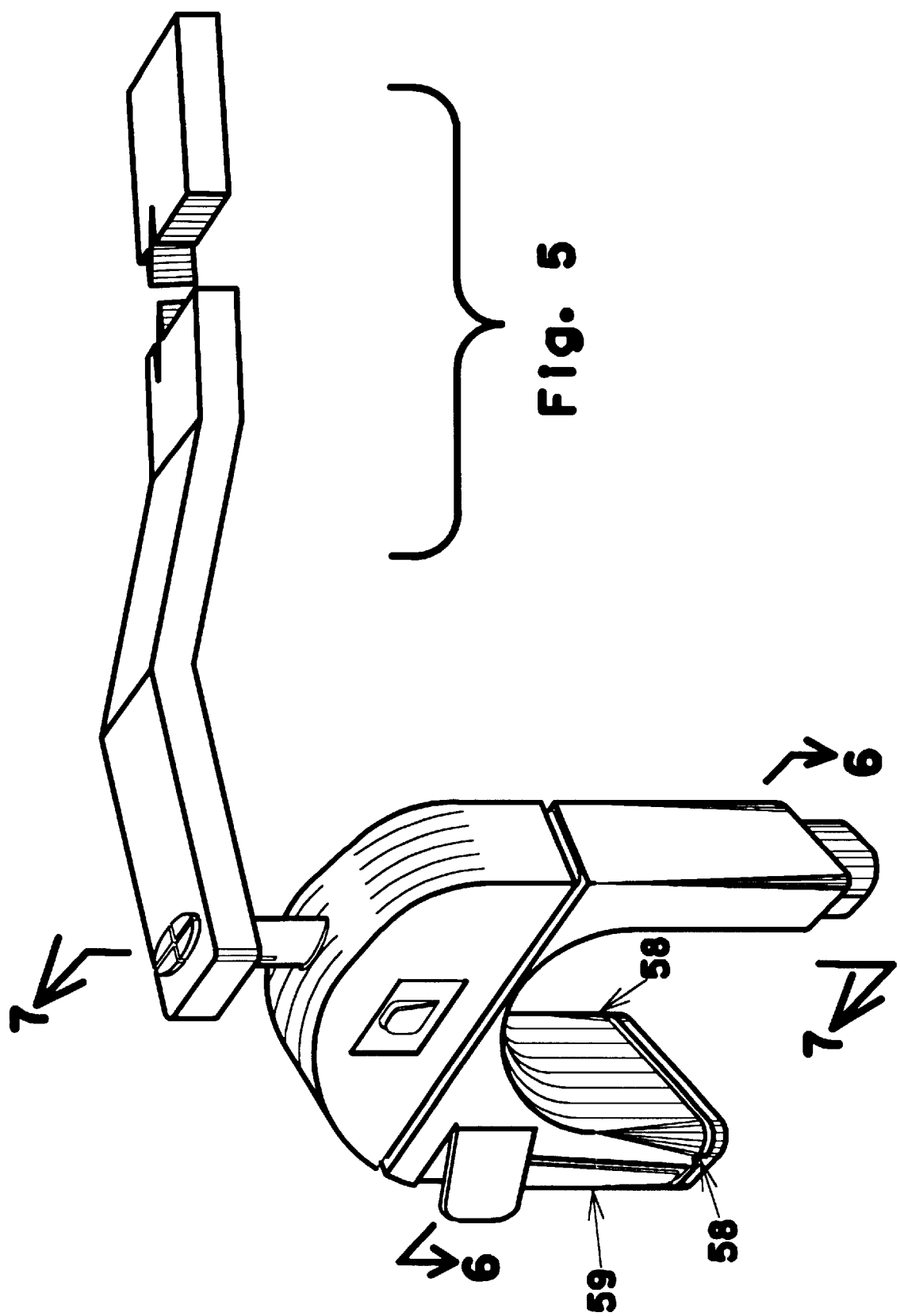
FIG. 5 is a perspective view of the second variation of the invented device.
Figure 6:
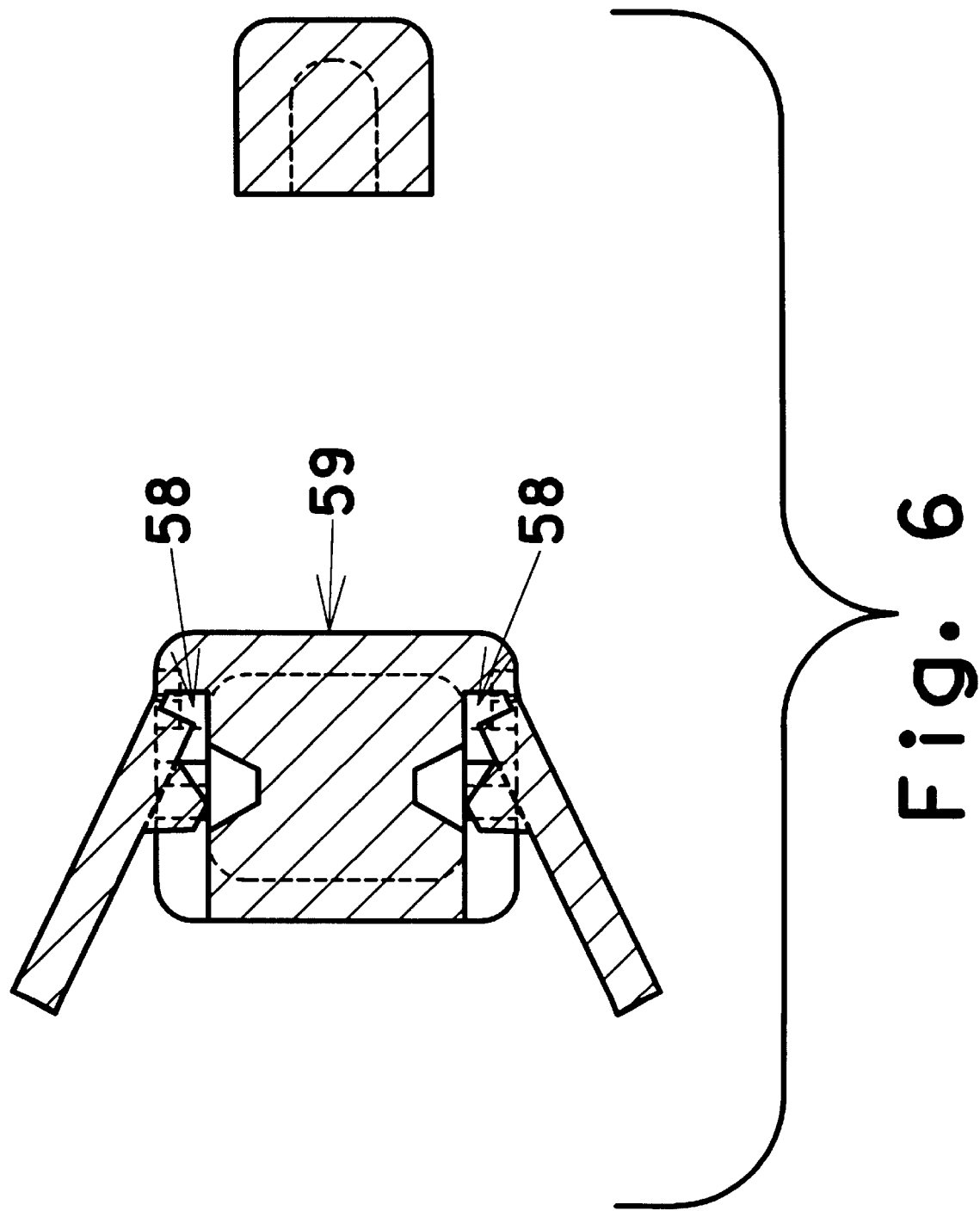
FIG. 6 is a sectional view of the device shown in FIG. 5.
Figure 7:
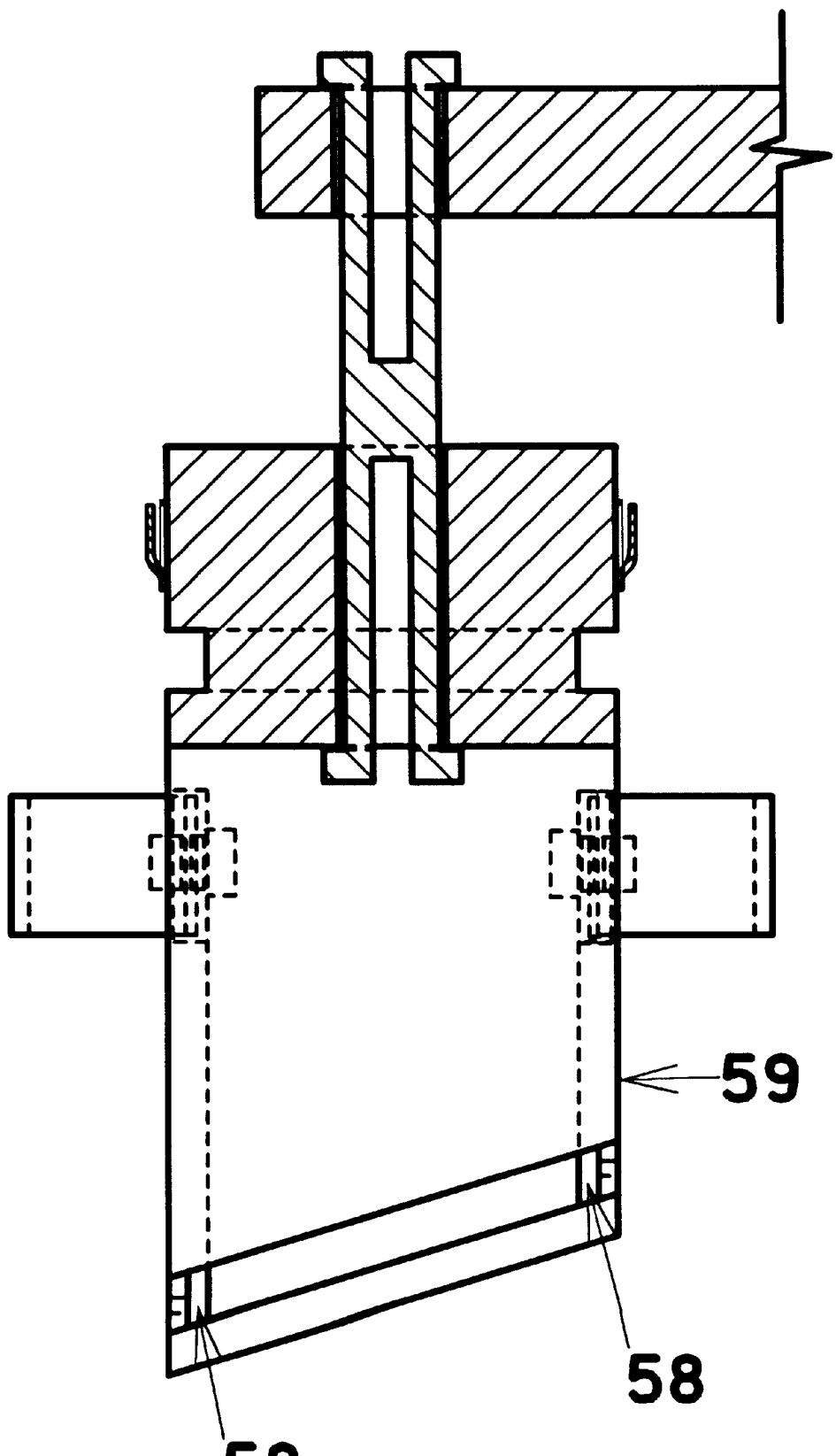
FIG. 7 is an another sectional view of the device shown in FIG. 5.
Figure 8:
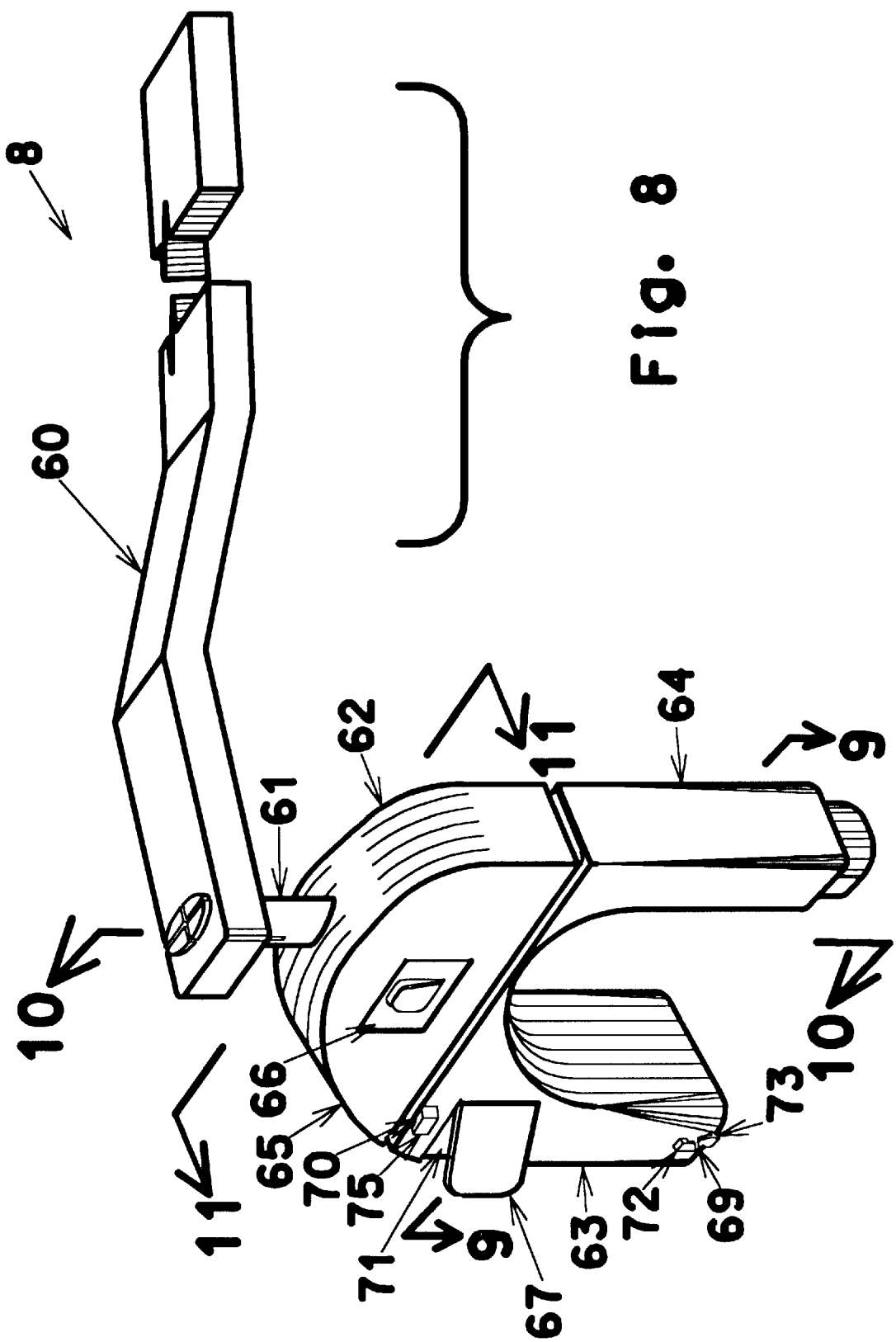
FIG. 8 is a perspective view of the third variation of the invented device.
Figure 9:
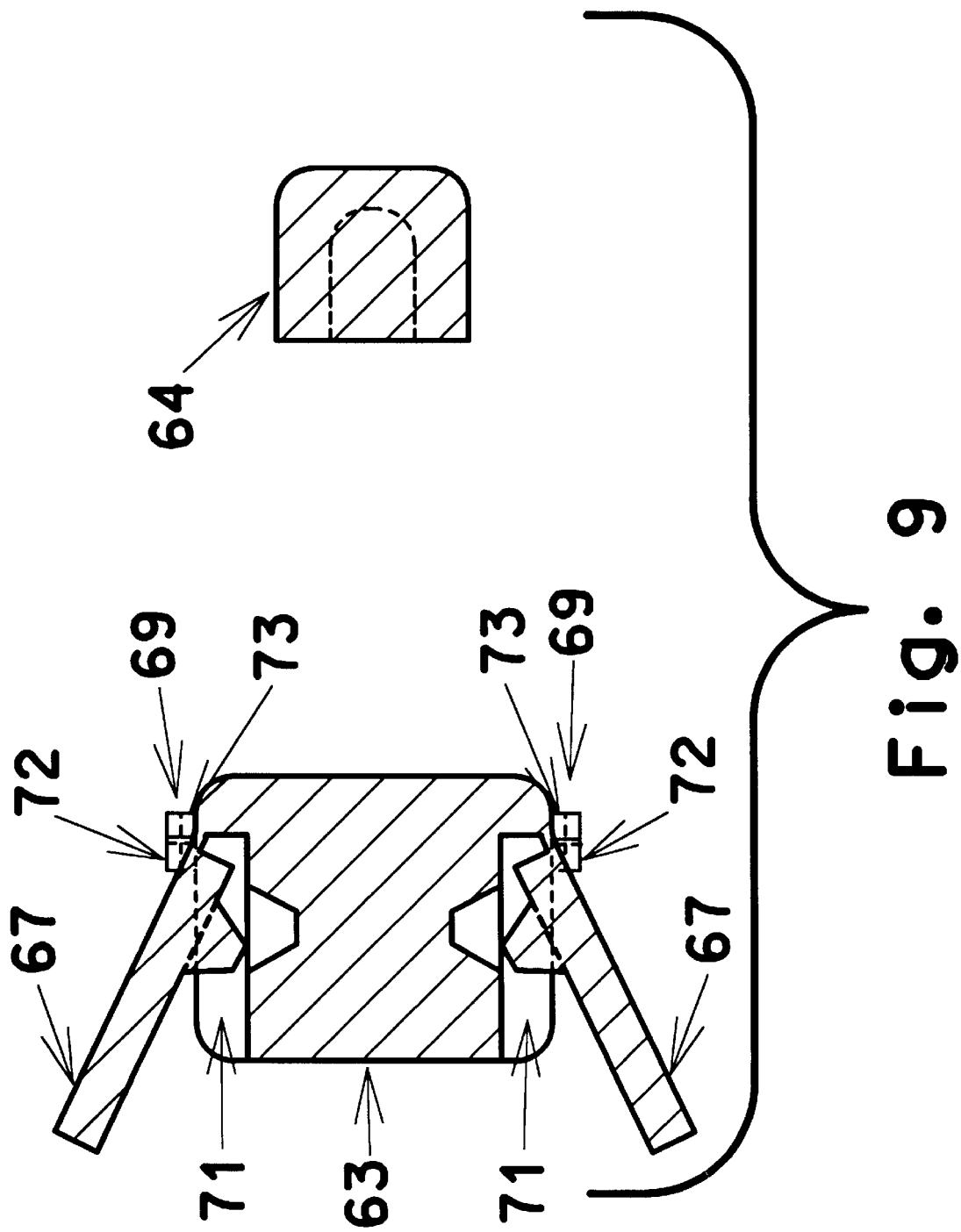
FIG. 9 is a sectional view of the device shown in FIG. 8.
Figure 10:
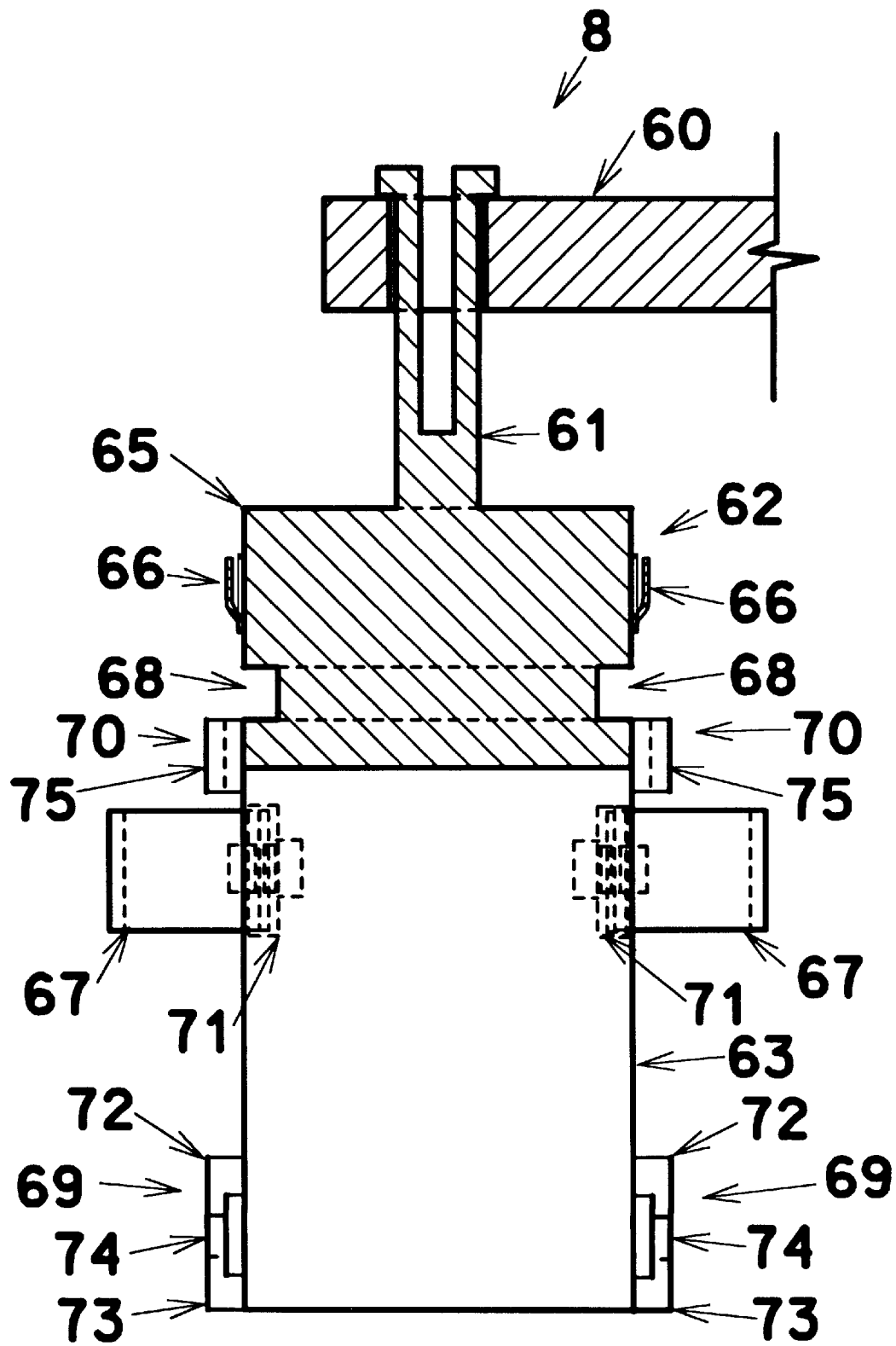
FIG. 10 is an another sectional view of the device shown in FIG. 8.
Figure 11:
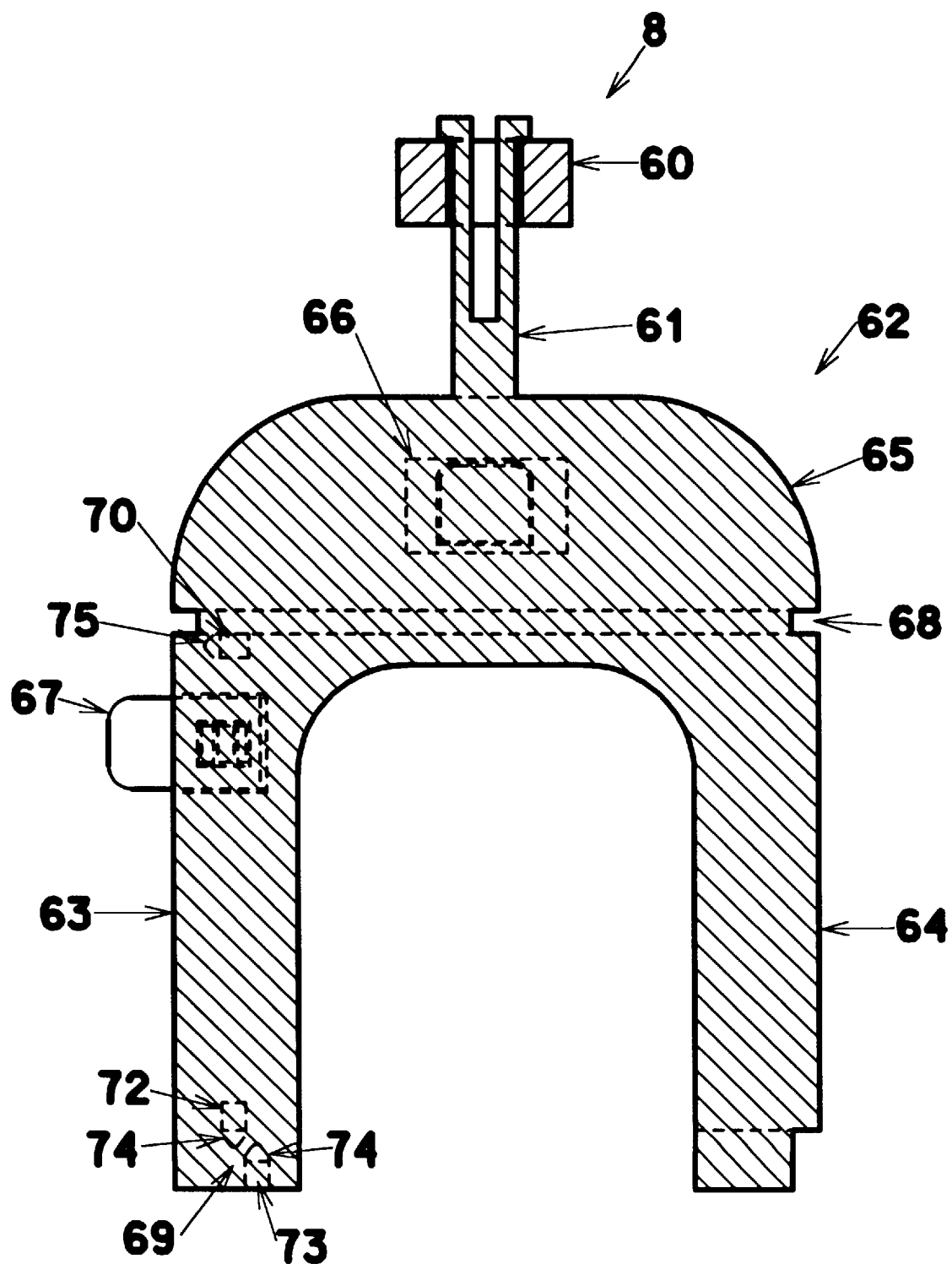
FIG. 11 is the other sectional view of the device shown in FIG. 8.

Referring to FIGS. 5, 6 and 7, the second variation of the invented dental floss applicator has the same components as these for the first variation which were described in the previous paragraphs. Basically, the two variations are the same except that in the first variation the plane delineated by the dental floss is perpendicular to its two legs while that of the second variation slants to the legs. This deference can be viewed easily when comparing between FIGS. 7 and 3. In FIG. 3, the two spaces 47 on both sides of the wide leg 35 is on the plane which is perpendicular to the edges of the wide leg. In FIG. 7, the two spaces 58 on both sides of the wide leg 59 is on the plane which is not perpendicular to the edges of the wide leg. The dental floss can be restricted by the spaces so that the plane they form is the same at those delineated by the spaces, either 47 or 58.

Referring to FIGS. 8 through 11, the third variation of the invented dental floss applicator 8 consists of a handle 60 and an applicator head 62.

The handle 60 is the same as those described for the first and the second variations of the invented dental floss applicators.

The applicator head 62 consists of a wide leg 63, a narrow leg 64, a base 65, one or two cutters 66, two lockers 67, a floss holder 68, a pair of floss guard 69, a connection rod 61, and a pair of floss guide 70. The narrow leg, the base, the cutters, the lockers, and the floss holder are similar to those of the first and second variations of the invented devices.

The wide leg 63 is the wider leg of the "U"-shaped applicator head while the narrow leg 64 is the narrower one. The wide leg is a leg that has the pair of floss guard 69 near its bottom rim, the pair of floss guides 70 on its upper portion, the two lockers 67, and a pair of recessed area 71 near its top where the wide leg joins with the base 65. The recessed area is similar to this for the first and the second variations of the invented devices.

The floss guards are on two opposite narrow sides of the wide leg. The floss guard consists of two blocks, the upper block 72 and the lower block 73. Both of them are blocks that extrude from the side walls of the wide leg. Each of them has a plate 74 that extrudes sideways from its main body. The plate forms an overhanging portion of the block. The two overhanging plates of the blocks face towards each other. The edges of the plates of the upper block and the lower block are offset so that a gap exists between the edges of the two plates. The frontal and the side edges of the plates of the lower block and the upper block form a "S" shape.

The floss guide 70 is an extruding block that is similar to the upper bock 72 or the lower block 73 of the floss guards. The extruding plate 75 of the floss guide faces away from the narrow leg.

The connection rod is a short rod which extrudes from the arm of the "U"-shaped object of the applicator head. The free end of the connection rod has an enlarged split end that can engage and connect with a hole in the handle.

Figure 12:
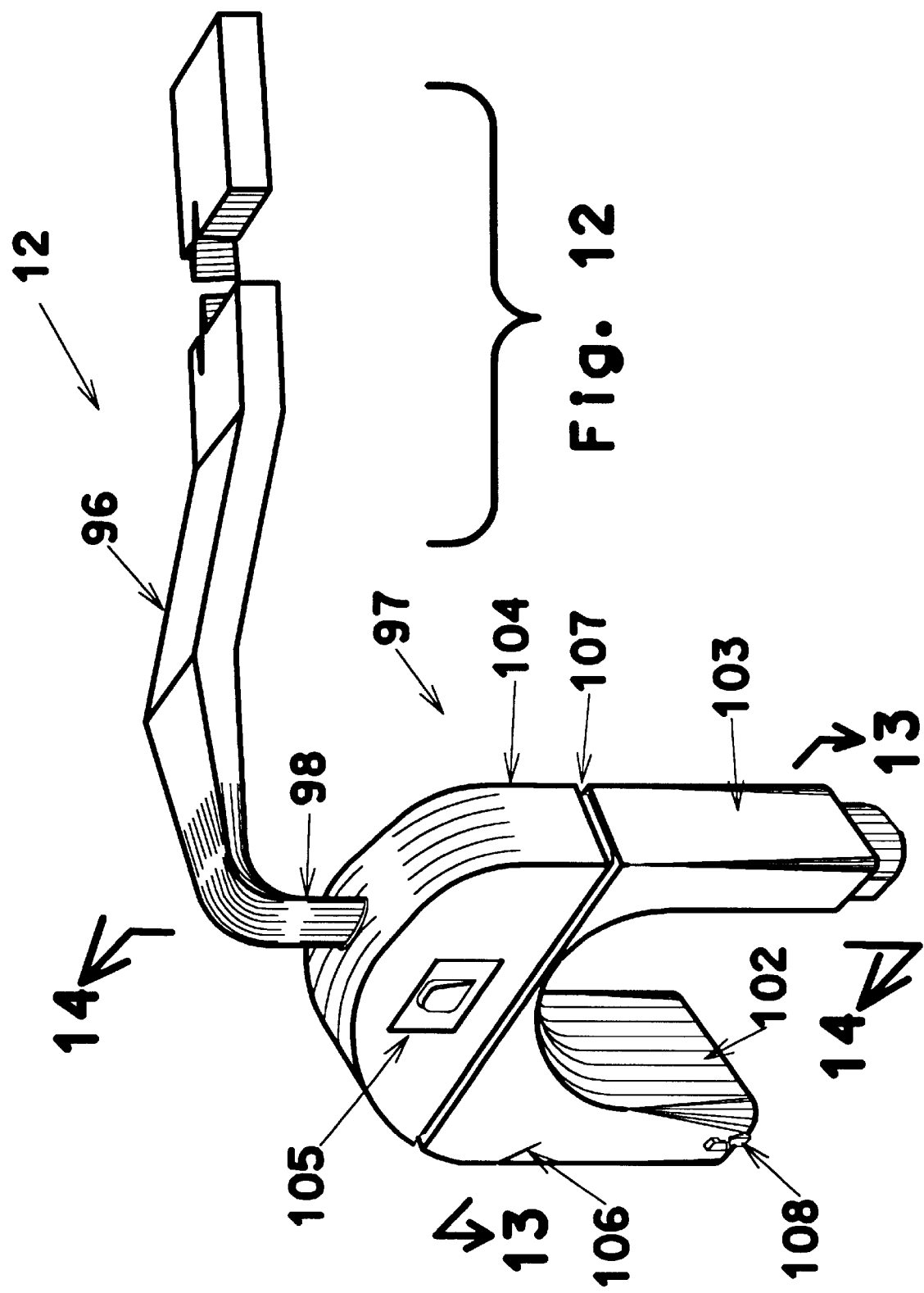
FIG. 12 is a perspective view of the fourth variation of the invented device.
Figure 13:
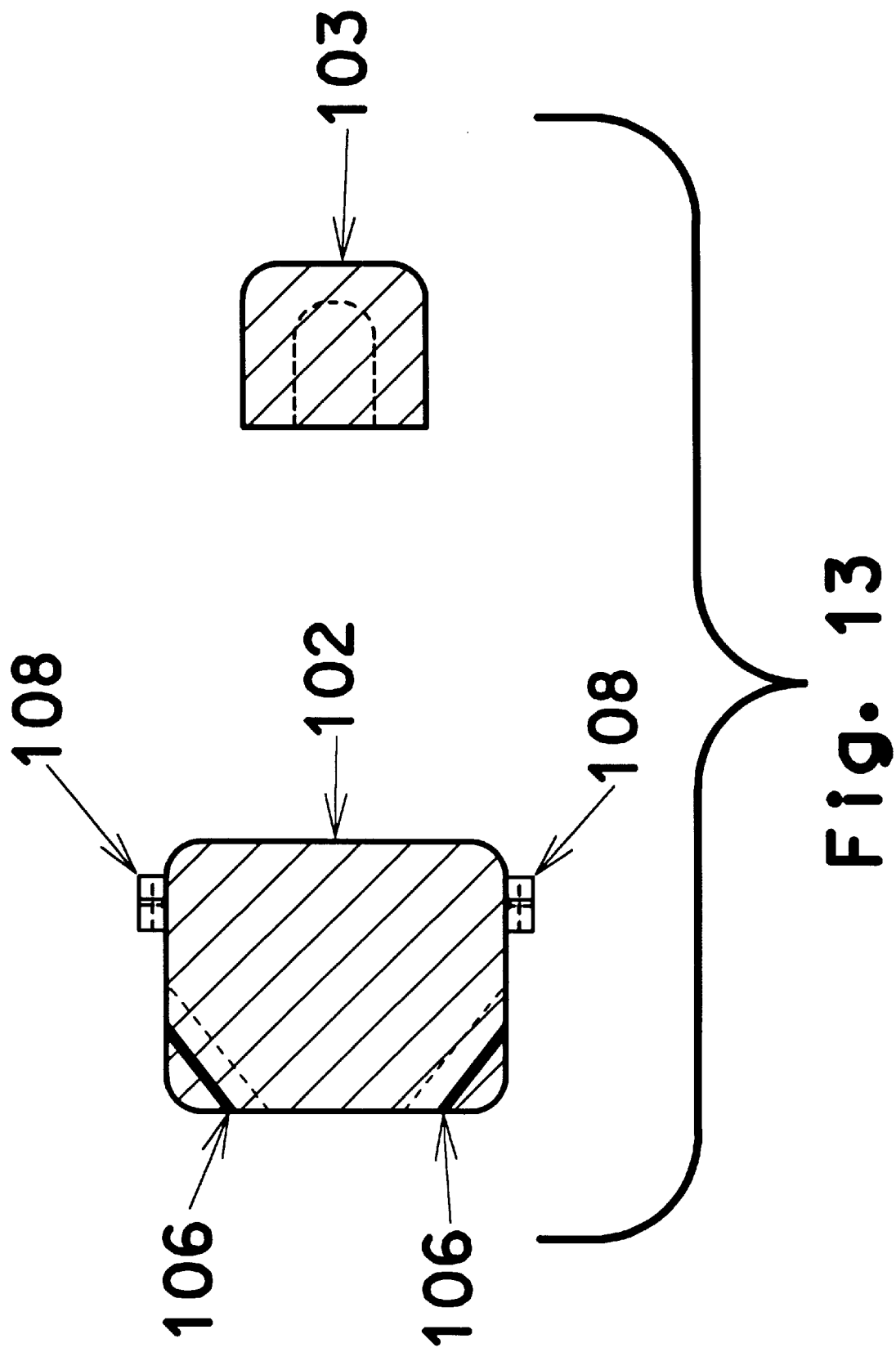
FIG. 13 is a sectional view of the device shown in FIG. 12.
Figure 14:
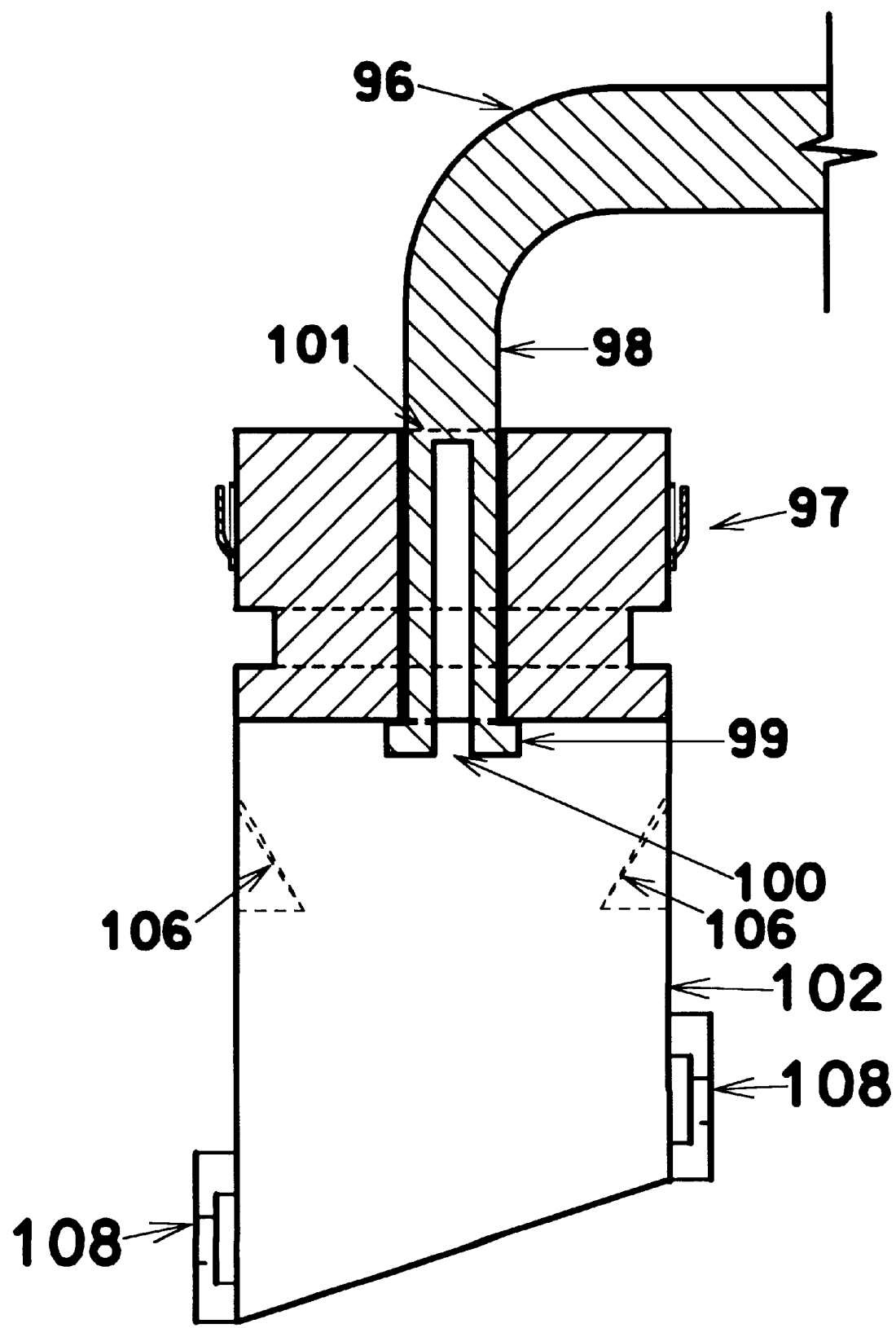
FIG. 14 is an another sectional view of the device shown in FIG. 12.
Figure 15:
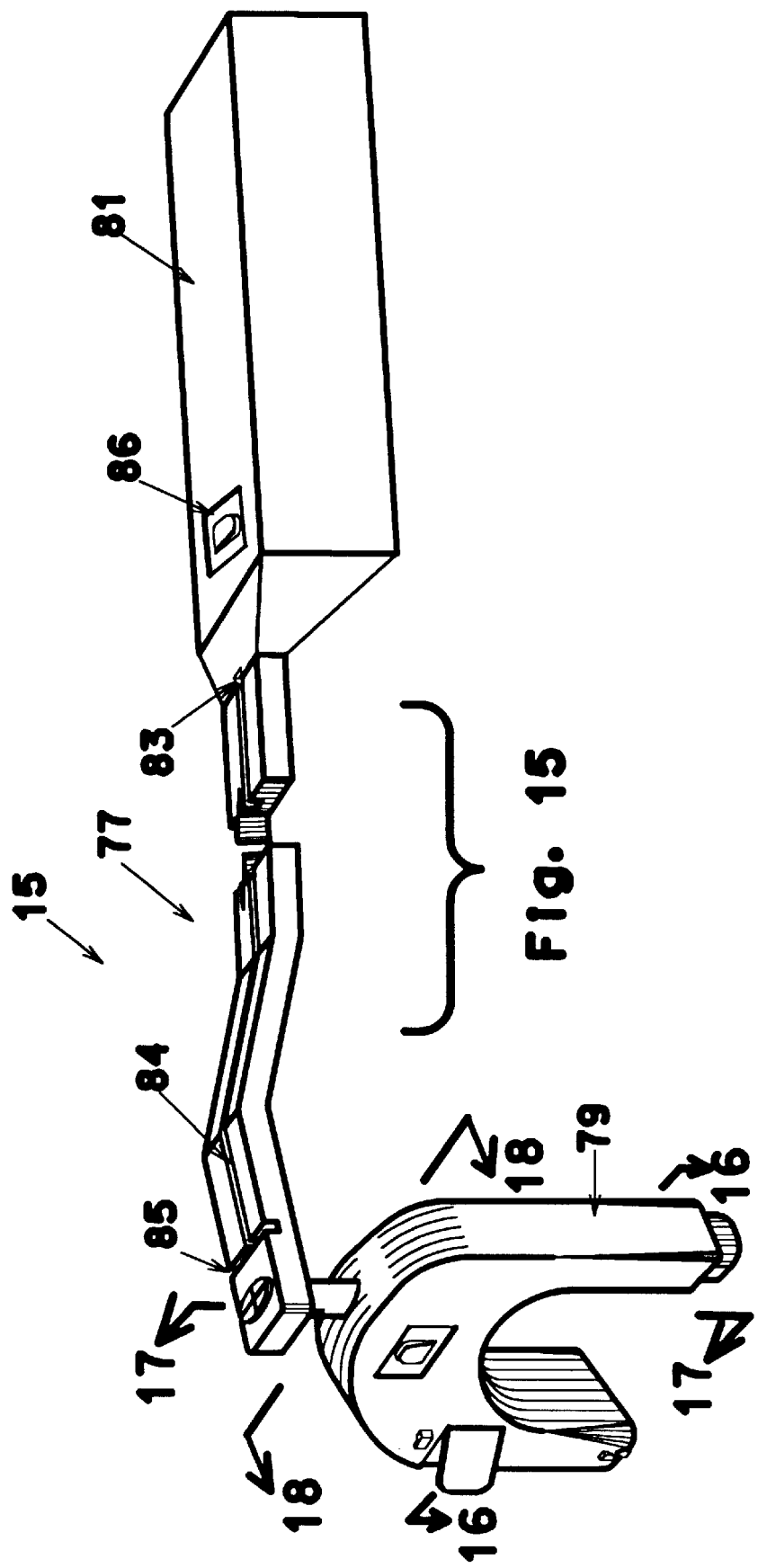
FIG. 15 is a perspective view of the fifth variation of the invented device.
Figure 16:
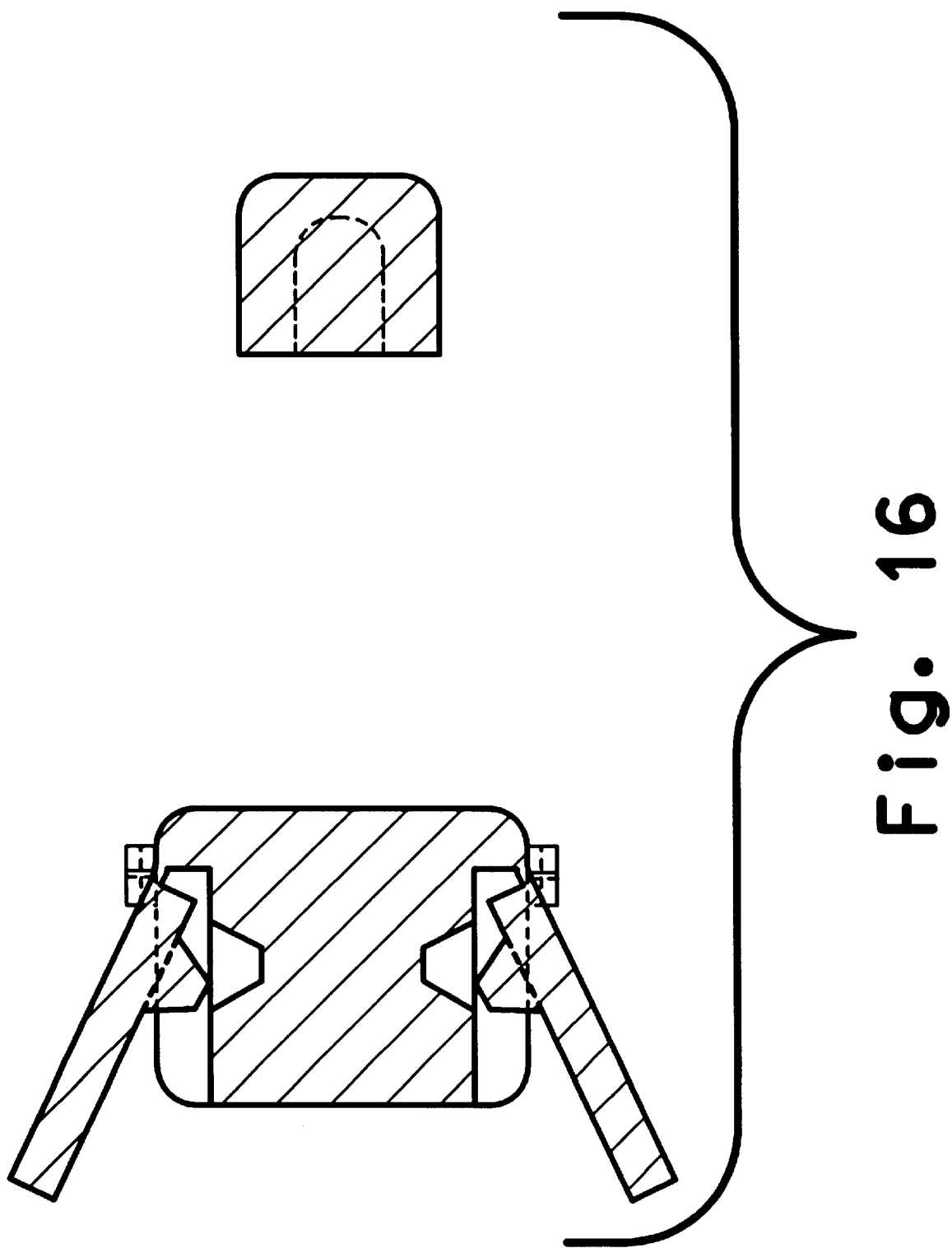
FIG. 16 is a sectional view of the device shown in FIG. 15.
Figure 17:
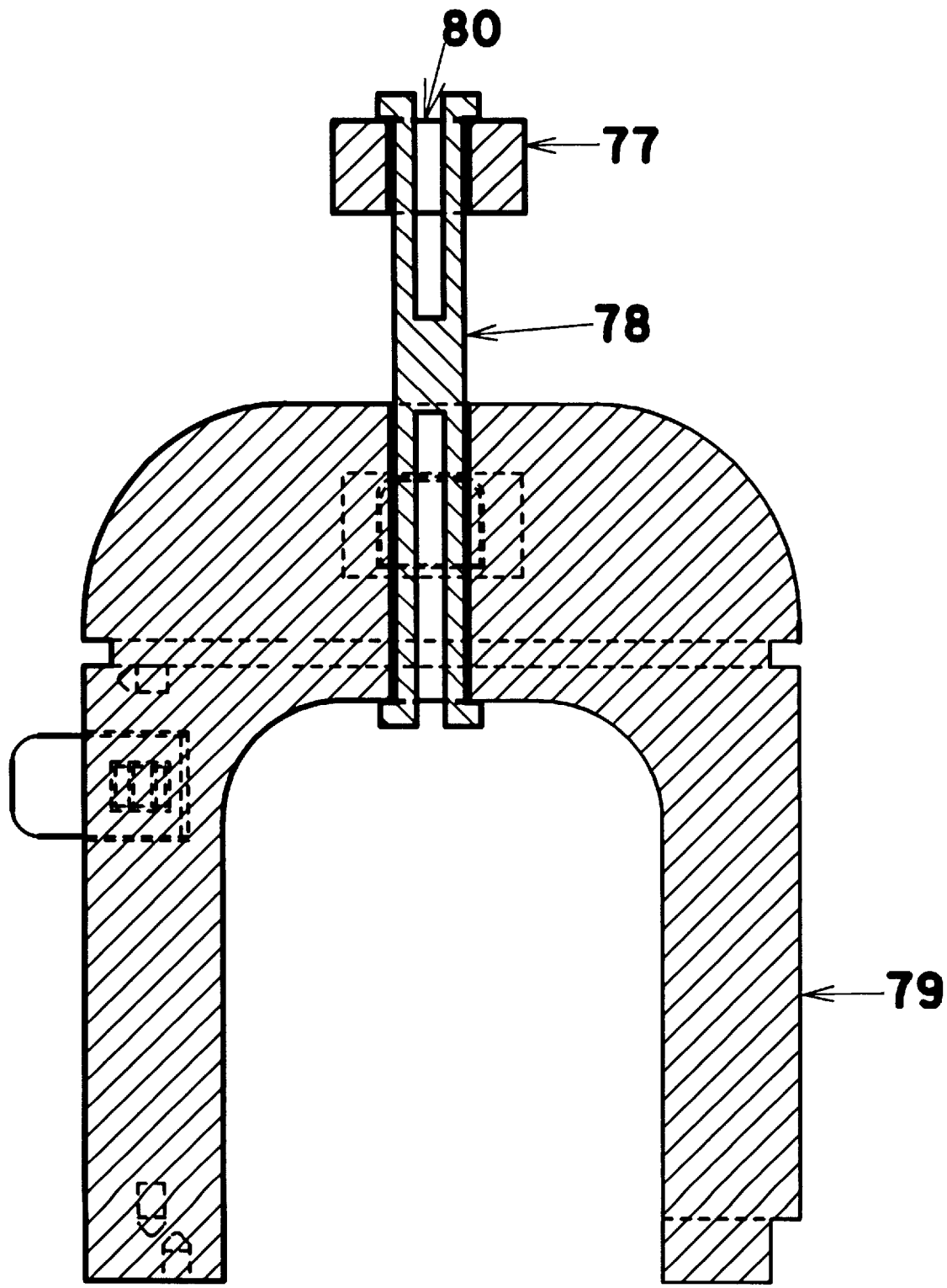
FIG. 17 is an another sectional view of the device shown in FIG. 15.
Figure 18:
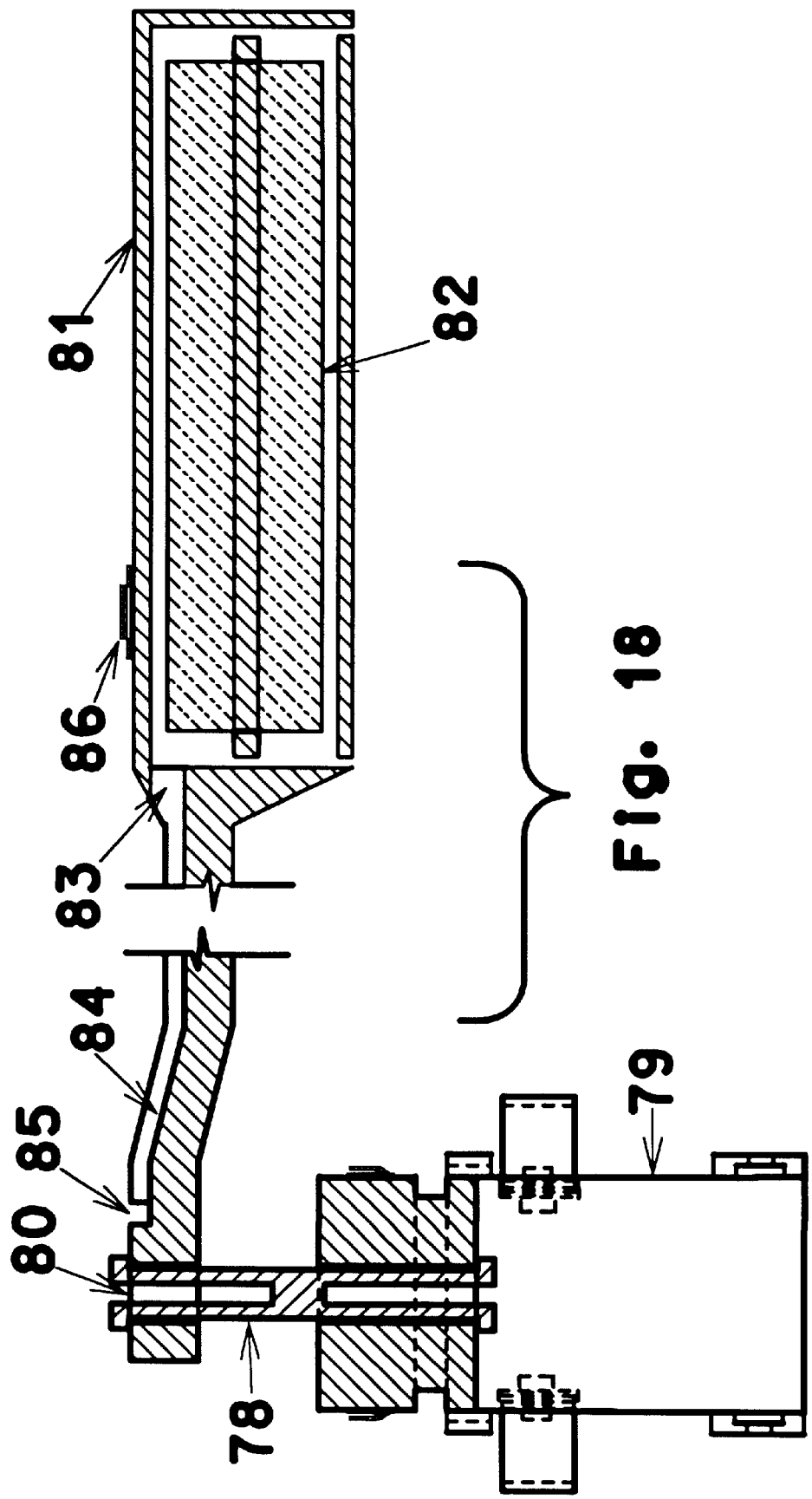
FIG. 18 is the other sectional view of the device shown in FIG. 15.

Referring to FIGS. 12, 13 and 14, the fourth variation of the invented dental floss applicator 12 consists of a handle 96 and an applicator head 97.

Similar to the other variations of the invented devices, the applicator head 97 consists of a wide leg 102, a narrow leg 103, a base 104, one or two cutters 105, two lockers 106, a floss holder 107, and a pair of floss guard 108. The wide leg, the narrow leg, the base, the cutters, the floss holder, and the floss guard are similar to those of the first, the second and/or the third variations of the invented devices. The locker 106 is wedge shaped deep cut on a corner of the wide leg. The locker is deep and narrow enough such that the dental floss can be retained in its deep cut.

The handle is an elongated object that can be held comfortably by a hand. A bent connector 98 is at one end of the handle. The bent connector has a sharp angle with respect to the main body of the handle. The bent connector is a rod with split enlarged end 99 and with hollow center 100 near its end. The end of the bent connector penetrates and engages with the hole 101 of the base of the applicator head. The applicator head can rotate around the axis of the bent connector.

Similar to the applicator head of the second variations of the invented devices and referring to FIGS. 12, 13 and 14, the plane delineated by the dental floss for the applicator head 97 of the fourth variation slants to the plane formed by the edges of the legs. This mean that, referring to FIG. 14, the two floss guards 76 on both sides of the wide leg 77 are on a plane that is not perpendicular to the edges of the wide leg. The dental floss can be restricted by the floss guards so that the plane they form is the same as those delineated by the floss guards.

Referring to FIGS. 15, 16, 17 and 18, the fifth variation of the invented dental floss applicator 15 consists of a handle 77, a connector 78, and an applicator head 79.

The connector 78 is the same as this for the first, the second, or the third variations of the invented devices. The applicator head 79 is almost the same as this for the first and the second or the third variations of the invented devices. The only difference between this applicator head 79 and those for the other variations is that there is no floss holder groove for this applicator head 79. Therefore, the applicator head 79 may optionally consist of a wide leg, a narrow leg, a base, one or two cutters, two lockers, and one or two floss guide; similar to those of the first and the second variations of the invented devices. The applicator head 79 may also optionally consist of a wide leg, a narrow leg, a base, one or two cutters, two lockers, a pair of floss guard, and a pair of floss guide; similar to those of the third and the fourth variations of the invented devices.

The handle is an elongated object that can be held comfortably by a hand. A hole 80 is located near one end of the handle. A floss holder 81 is on the other end of the handle. This floss holder is a container in which a reel of dental floss 82 can be stored. There is an opening 83 on a side wall of the floss holder. The handle has a floss groove 84 that is a groove longitudinally on most part of the handle. One end of the floss groove connects with the opening 83. The other end of the floss groove connects to a "T"-groove 85 that is a groove across the handle, A cutter 86 is on the floss holder. This cutter is similar to those cutters described previously.

Referring to FIGS. 29 through 32, the sixth variation of the invented dental floss applicator 109 consists of a handle 110, a connector 111, and an applicator head 112.

The handle 110 and the connector 111 are the same as these for the first, the second, the third or the fifth variations of the invented devices. Similar to the other variations, the applicator head 112 consists of a wide leg 113, a narrow leg 114, a base 115, one or two cutters 116, two lockers 117, and a floss holder 118. The wide leg, the narrow leg, the base, the cutters, and the floss holder are similar to those of the other variations of the invented devices. Unlike for the other variations, the wide leg 113 does not have any aforementioned floss guard or floss guides. The lockers 117 are similar to these of the first variation of the invented device except that the plates for the lockers 117 are longer than those for the first variation.

Figure 19:
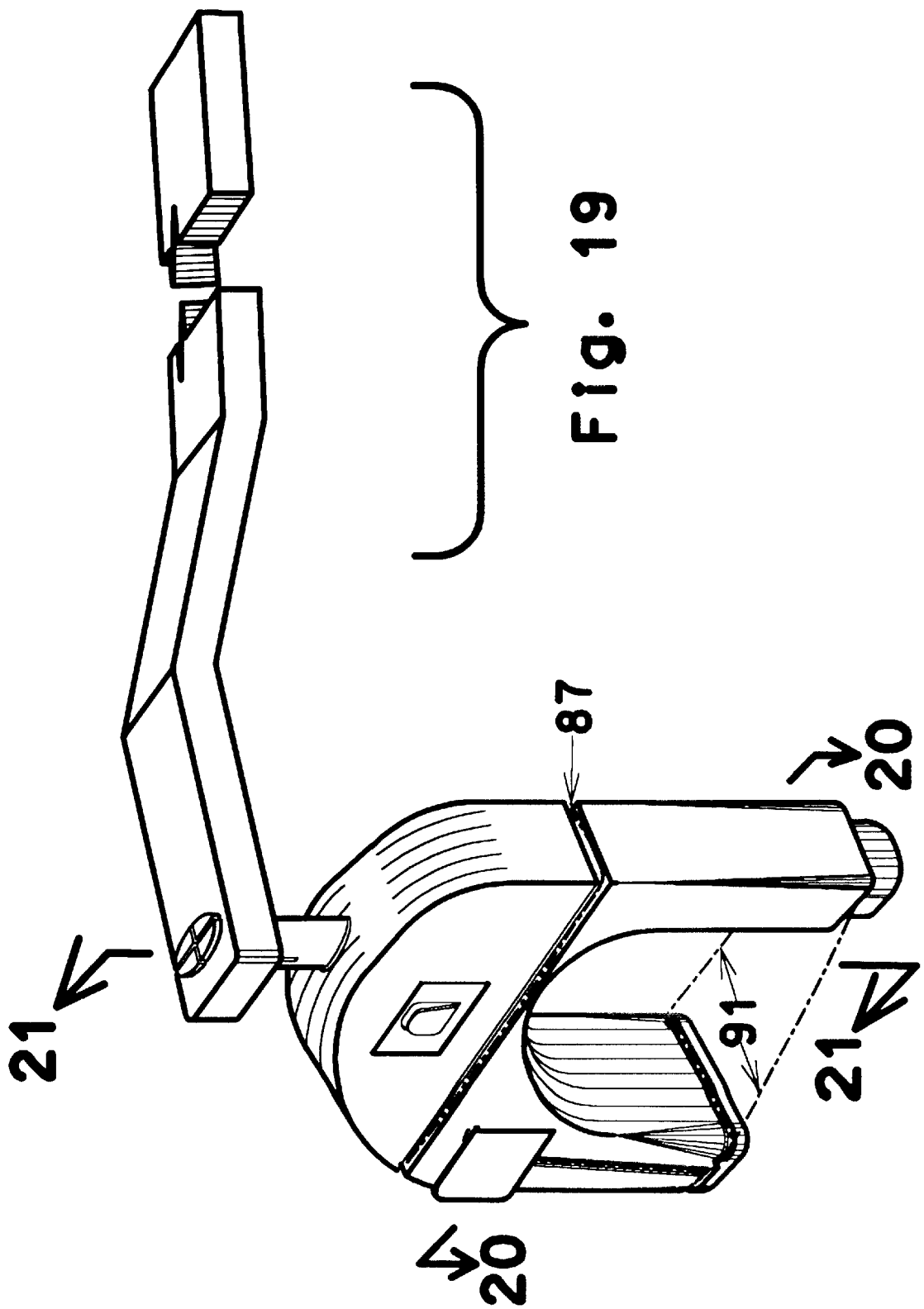
FIG. 19 is a perspective view of the device shown in FIG. 1.
Figure 20:
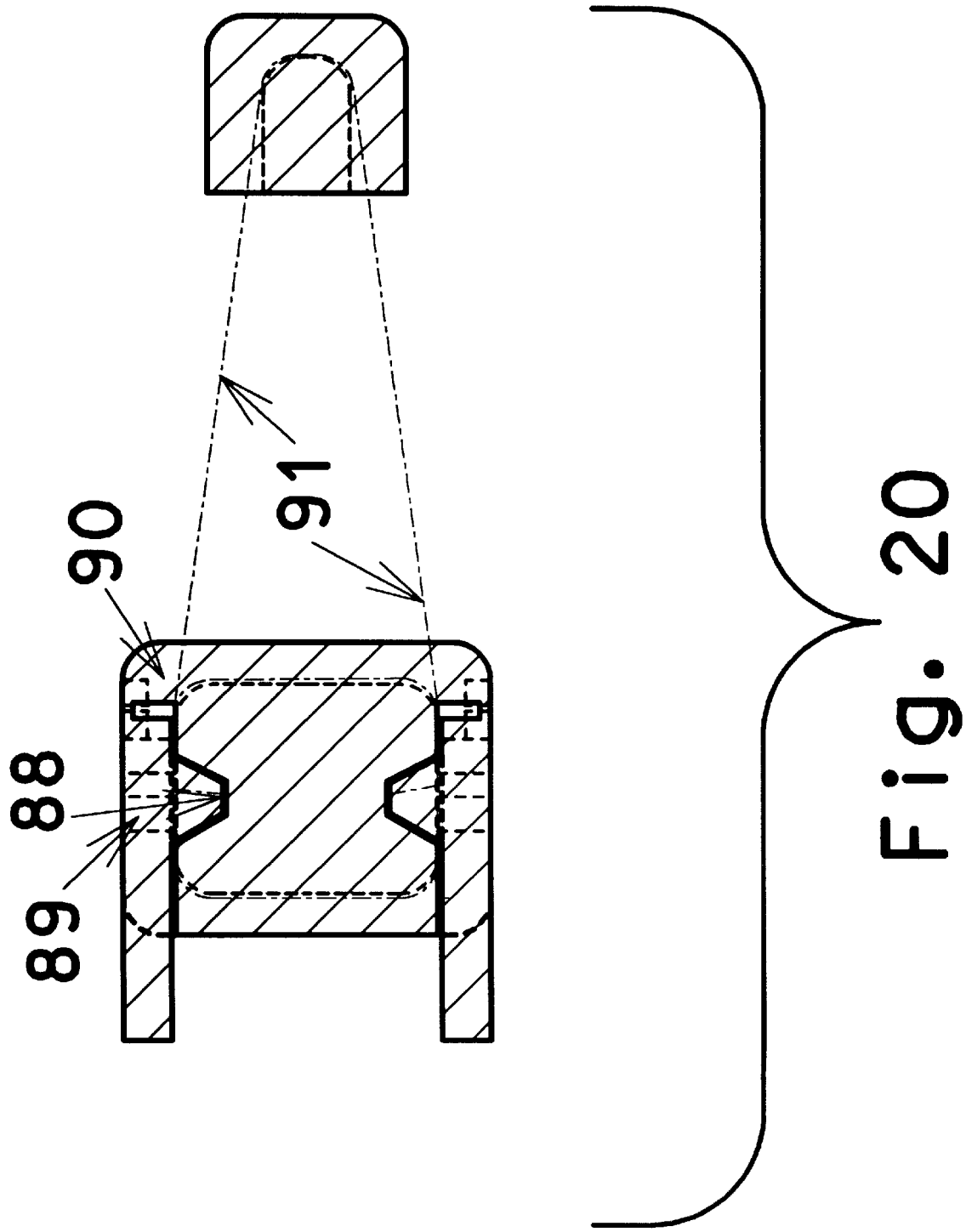
FIG. 20 is a sectional view of the device shown in FIG. 19 that has an attached dental floss line.
Figure 21:
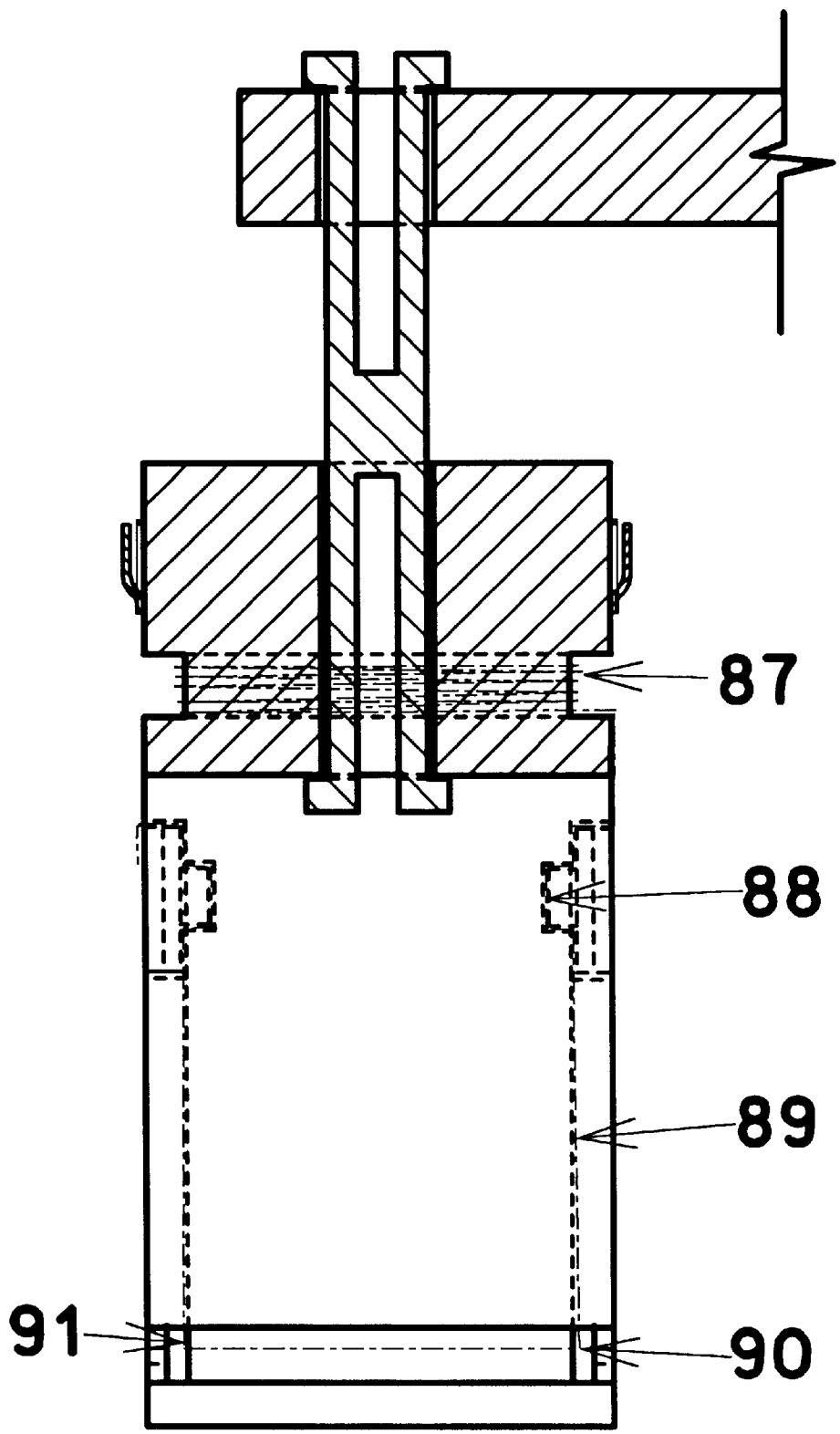
FIG. 21 is an another sectional view of the device shown in FIG. 19 that has an attached dental floss line.

Referring to FIGS. 19, 20 and 21, in preparations for using the first and the second variations of the invented device, the user firstly obtains a piece of dental floss of adequate length. The user then winds the majority of the dental floss around the base of the applicator head in its floss holder (87, FIGS. 19 and 21). The user then put the un-winded dental floss across the locker with the dental floss passing between the key and the keyhole. The user then closes the locker so that the dental floss is locked in place by the key and the keyhole (88, FIGS. 20 and 21). The user then routes the remaining dental floss down through the floss guide (89, FIGS. 20 and 21) to the floss groove. The user then guides the dental floss through the gap between the edges of the two plates of a floss guard and puts the dental floss through the space between the floss guard and the end wall of the floss groove (90, FIGS. 20 and 21 ) Then the user guides the dental floss around the frontal portion of the extruding block of the narrow leg and back to the other floss guard (91, FIGS. 19, 20 and 21). The user then brings the dental floss through the floss guard, the floss groove and the floss guide to the locker. The dental floss will be guided through the locker with the dental floss passing through the key and the keyhole. Then the user closes the locker so that the dental floss will be locked in place. The user has the option to bring the dental floss in the floss groove around the wide leg many laps before brining it back to the locker via the floss guide.

The preparations for using the third variation of the invented devices is similar to those described for the first and the second variations of the invented devices. In the preparations, the user firstly obtains a piece of dental floss of adequate length. The user then winds the majority of the dental floss around the base of the applicator head in its floss holder. The user then put the un-winded dental floss through the floss guide then across the locker with the dental floss passing between the key and the keyhole. The user then closes the locker so that the dental floss is locked in place by the key and the keyhole. The user then routes the remaining dental floss down along surface of the wide leg to the upper block of the floss guard. The user then guides the dental floss through the gap between the edges of the two plates of a floss guard and puts the dental floss through the space between the floss guard and the wall of the wide leg. Then the user guides the dental floss around the frontal portion of the extruding block of the narrow leg and back to the other floss guard. The user then brings the dental floss through the floss guard to the locker. The dental floss will be guided through the locker with the dental floss passing through the key and the keyhole. Then the user closes the locker so that the dental floss will be locked in place.

The preparations for using the fourth variation of the invented devices is similar to those described for the third variation of the invented devices. In the preparations, the user firstly obtains a piece of dental floss of adequate length. The user then winds the majority of the dental floss around the base of the applicator head in its floss holder. The user then put a un-winded dental floss's segment which is near the floss holder into the locker so that the dental floss can be locked in place by the wedge shaped slot of the locker. The user then routes the remaining dental floss down along surface of the wide leg to the upper block of the floss guard. The user then guides the dental floss through the gap between the edges of the two plates of a floss guard and puts the dental floss through the space between the floss guard and the wall of the wide leg. Then the user guides the dental floss around the frontal portion of the extruding block of the narrow leg and back to the other floss guard. The user then brings the dental floss through the floss guard to the locker to have the dental floss be locked in place.

In preparations for using the sixth variation of the invented devices, the user firstly obtains a piece of dental floss of adequate length. The user then winds the majority of the dental floss around the base of the applicator head in its floss holder. The user then put the un-winded dental floss across the locker with the dental floss passing between the key and the keyhole. The user then guide the dental floss to pass under the bottom edge of the plate of the locker. The user then closes the locker so that the dental floss is locked in place by the key and the keyhole. Then the user guides the dental floss around the frontal portion of the extruding block of the narrow leg and back to the other floss guard. The user then guides the dental floss through the bottom edge of the plate of the other locker. The dental floss will be guided through the locker with the dental floss passing through the key and the keyhole. Then the user closes the locker so that the dental floss will be locked in place.

Figure 22:
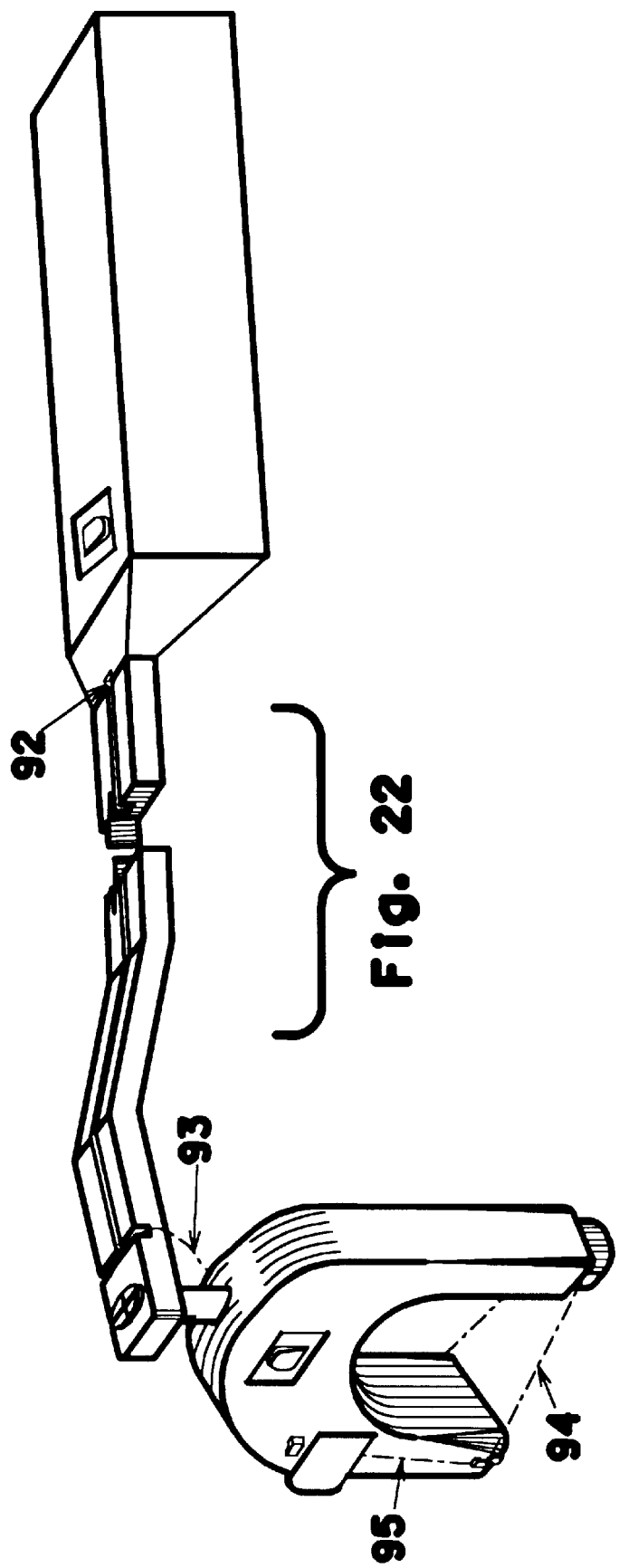
FIG. 22 is a perspective view of the device shown in FIG. 15.
Figure 23:
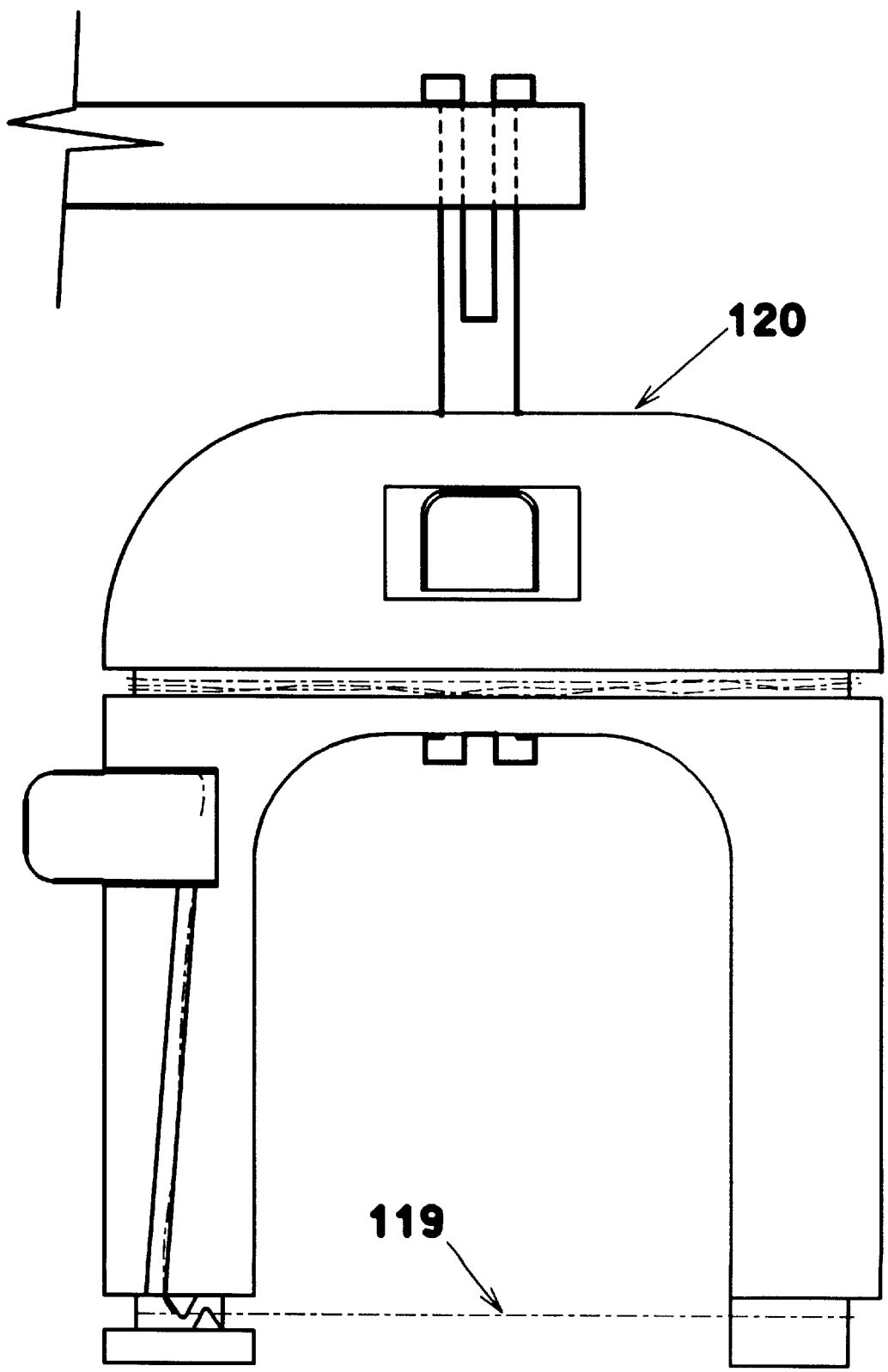
FIG. 23 is a schematic that shows that a line of dental floss is mounted on an invented device.

Referring to FIG. 22 for the preparation work in using the fifth variation of the invented devices. In FIG. 22, the applicator head similar to this for the third variation is shown. The user firstly pulls an adequate length of dental floss out of the floss holder through the opening (92, FIG. 22). The user then guides the dental floss through the floss groove and through the "T"-groove (93, FIG. 22). The user then put the dental floss through the floss guide then across the locker with the dental floss passing between the key and the keyhole. The user then closes the locker so that the dental floss is locked in place by the key and the keyhole. The user then routes the remaining dental floss down along surface of the wide leg to the upper block of the floss guard. The user then guides the dental floss through the gap between the edges of the two plates of a floss guard and puts the dental floss through the space between the floss guard and the wall of the wide leg. Then the user guides the dental floss around the frontal portion of the extruding block of the narrow leg and back to the other floss guard (94, FIG. 22). The user then brings the dental floss through the floss guard to the locker (95, FIG. 22). The dental floss will be guided through the locker with the dental floss passing through the key and the keyhole. Then the user closes the locker so that the dental floss will be locked in place.

Although FIG. 22 shows the applicator head similar to this for the third variation of the invented devices, the applicator heads similar to these of the other variations can be installed for the fifth variation of the invented devices. Previous paragraphs described the preparation work for such applicator heads. Therefore, these works are not repeatedly described herein.

Referring to FIGS. 23 through 28 for the descriptions of the uses of the invented device. Although the applicator head for the first variation of the invented devices are shown in the figures, the principle of using of the invented devices will be the same for other variations.

Figure 24:
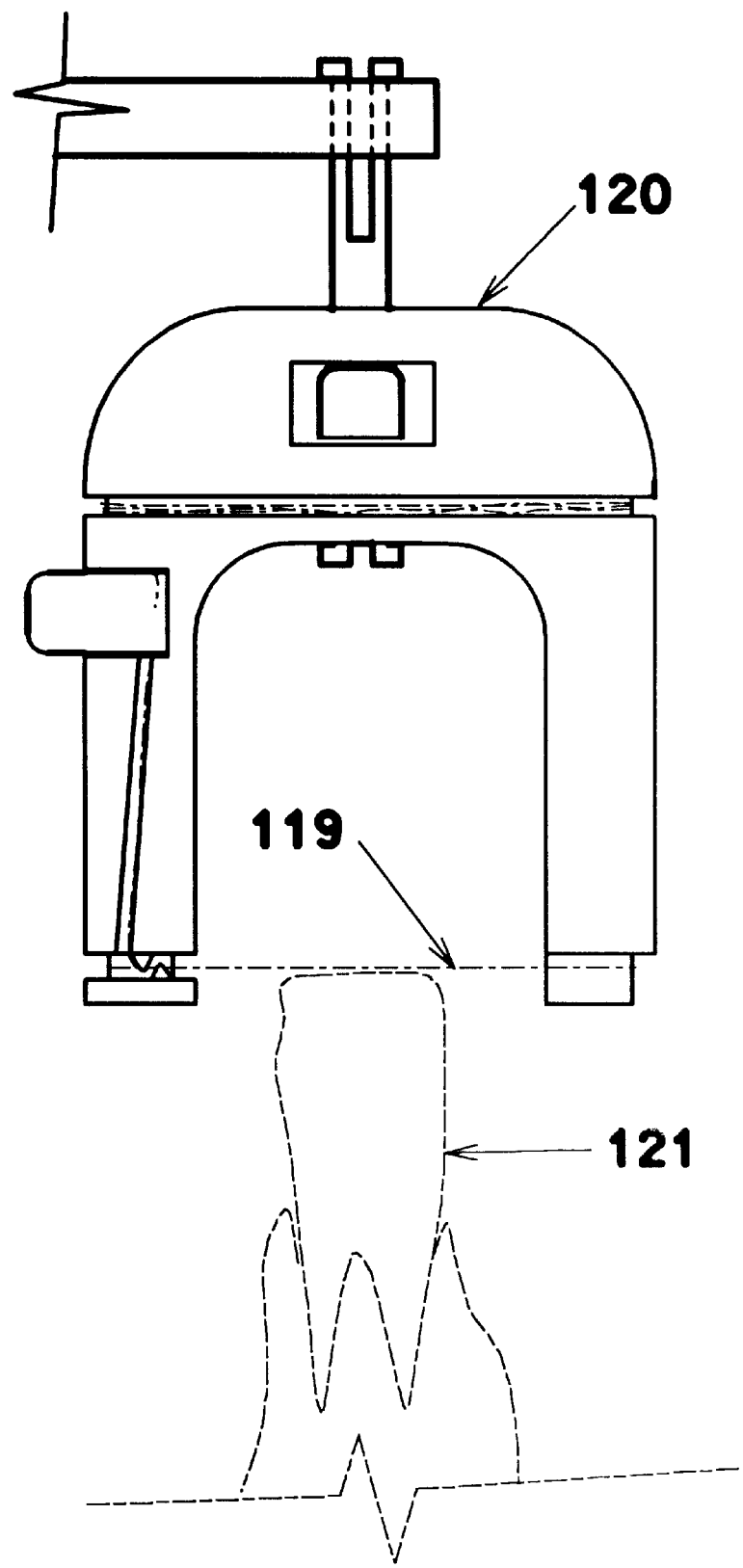
FIG. 24 is a schematic which shows that an invented device with mounted dental floss is about to lower between teeth.

After the preparation work and the dental floss (119, FIG. 23) is placed on the applicator head (120, FIG. 23), the applicator head will be put into a mouth with the dental floss placed above the gaps between teeth (121, FIG. 24). Since the sizes of teeth are different, the spacing between gaps on both sides of teeth are different. To ensure the dental floss is above a gap between teeth, the user adjusts the relative position of the applicator head with respect to a tooth. For a large tooth, the user will place the wide leg of the applicator head close to the tooth because the two lines of dental floss near the wide leg are separated further apart than those near the narrow leg. The two lines of the dental floss over there are separated wide enough so that they can be inserted into the gaps on both sides of a large tooth. For a small tooth, the user will place the narrow leg of the applicator head close to the tooth. The two lines of dental floss are apart closely enough so that they can be inserted into the gaps on both sides of a small tooth.

Figure 25:
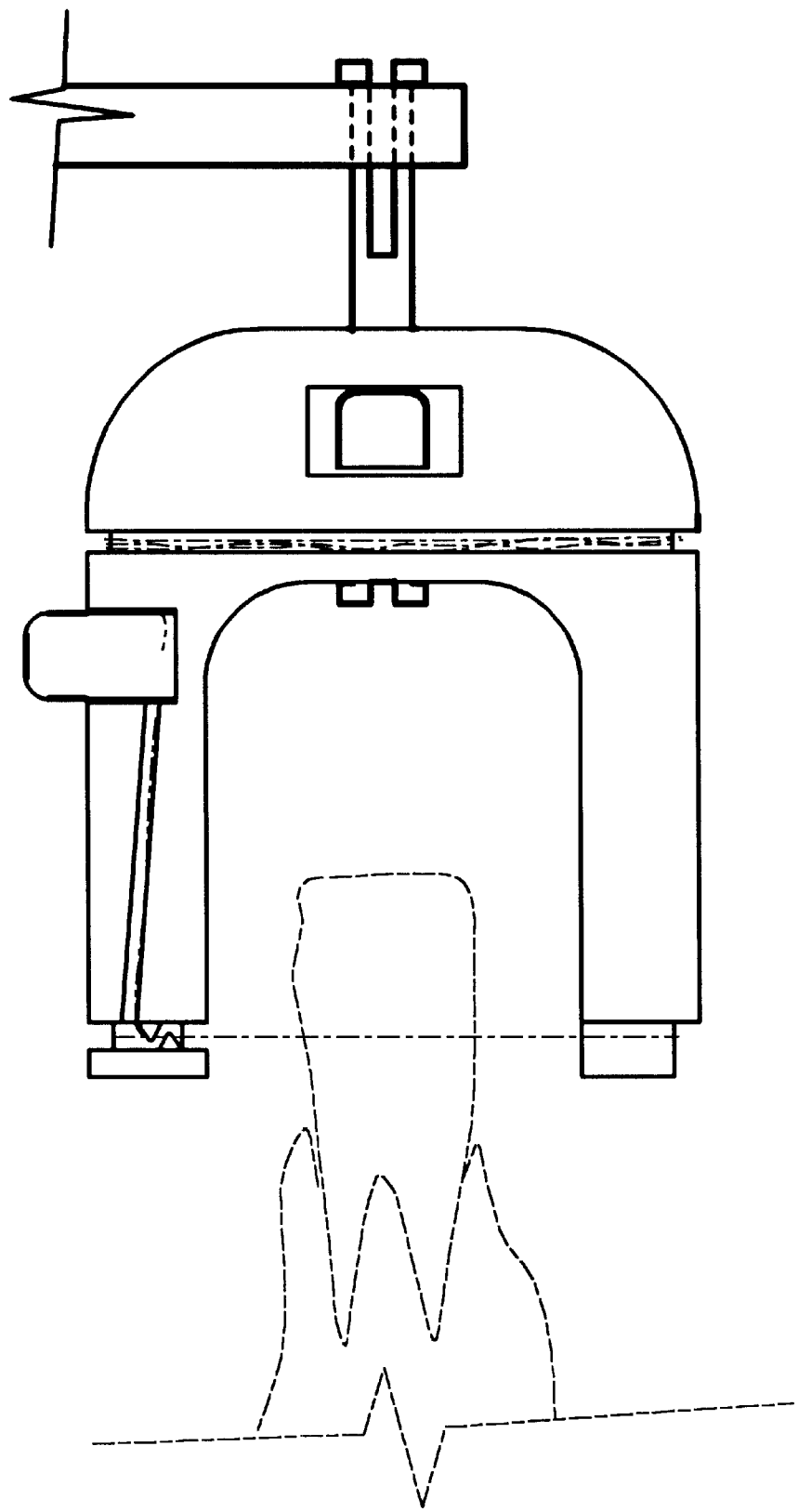
FIG. 25 is a schematic that shows that the mounted dental floss is lowered between teeth.

Referring to FIG. 25, the user will push the two lines of dental floss into the two gaps on both sides of a tooth. The larger cross-sectional area of the narrow leg than that of the extruding block will prevent the dental floss being pushed upwards into the narrow leg. The floss guards and the floss groove will also prevent the upward movements of the dental floss.

Figure 26:
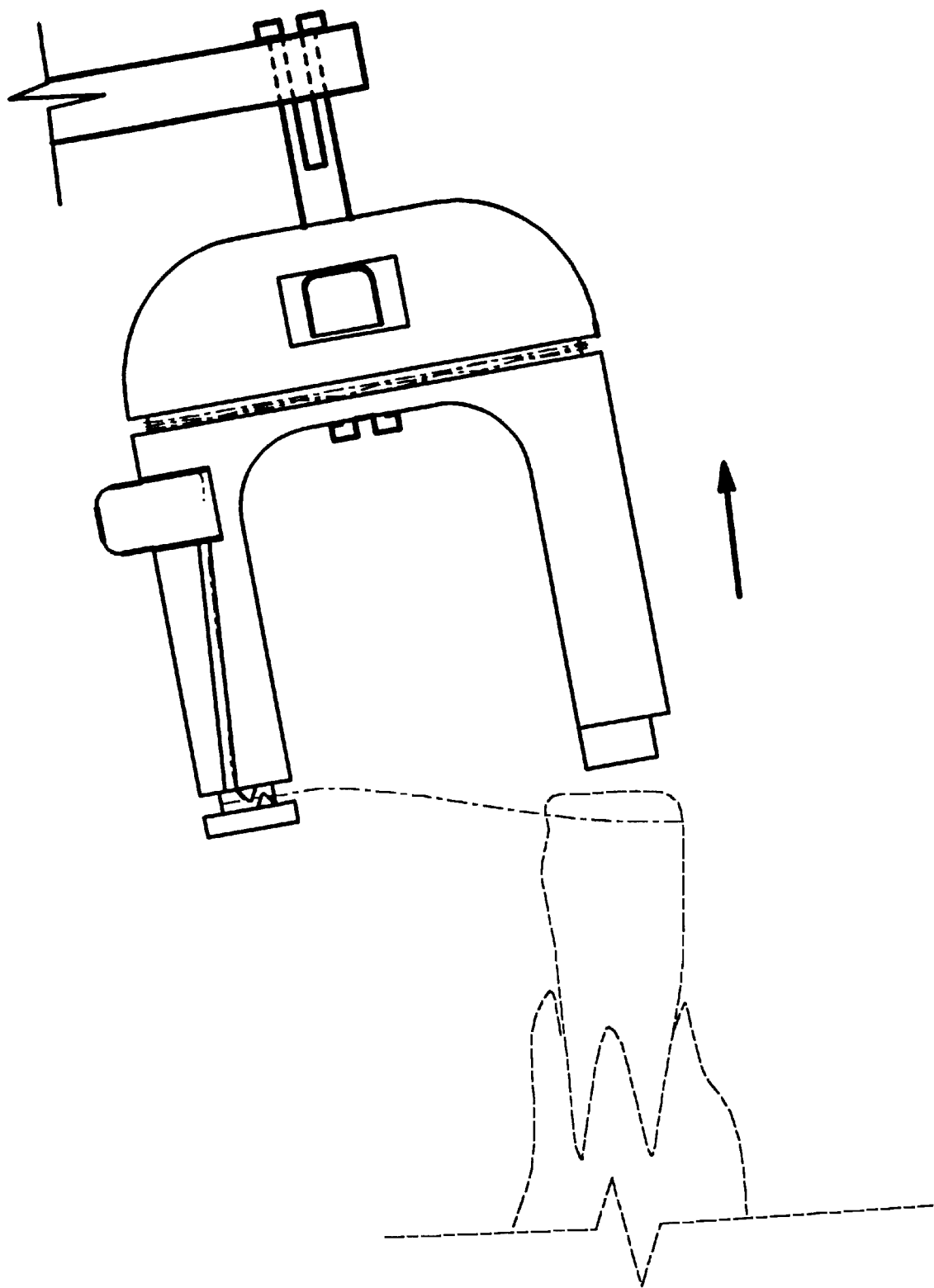
FIG. 26 is a schematic that shows that the invented device is raised from the teeth and the loop of the dental floss line remains between the teeth. The dental floss line is released from one leg of the invented device.

Referring to FIG. 26, after the two lines of the dental floss being pushed into the gaps between the teeth, the user will lift back the applicator head. Due to the fact that 1) the gap between two adjacent teeth has a wedge shape with a narrow gap on its top and 2) the dental flosses are pushed into the gaps, the dental flosses will be pulled off from the narrow leg when the applicator head is lifted. At this time, a loop of dental floss is left around three sides of a tooth.

Figure 27:
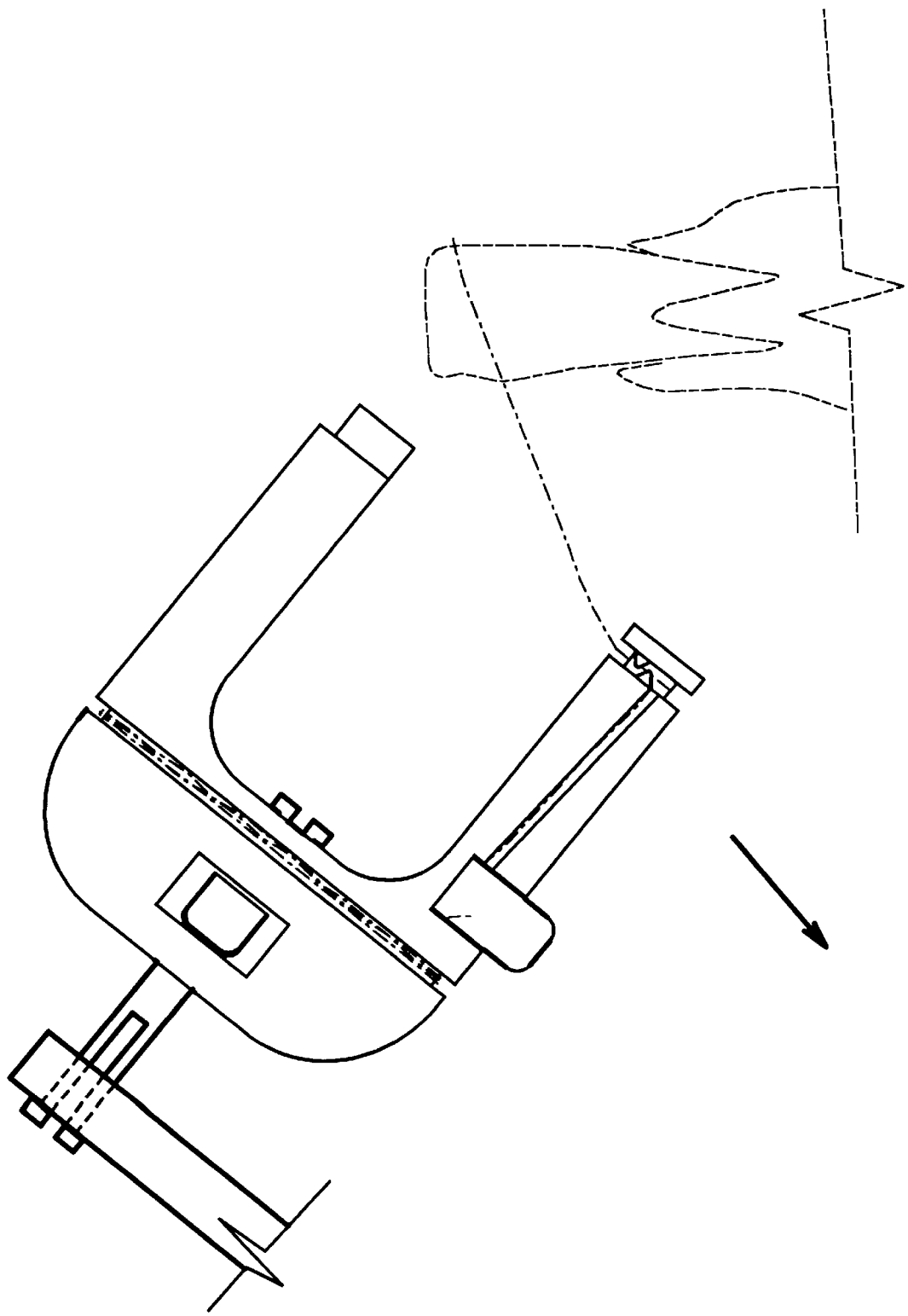
FIG. 27 is a schematic that shows that the invented device is moved downwards while the loop of the dental floss line scrubs downward of a surface of a tooth.
Figure 28:
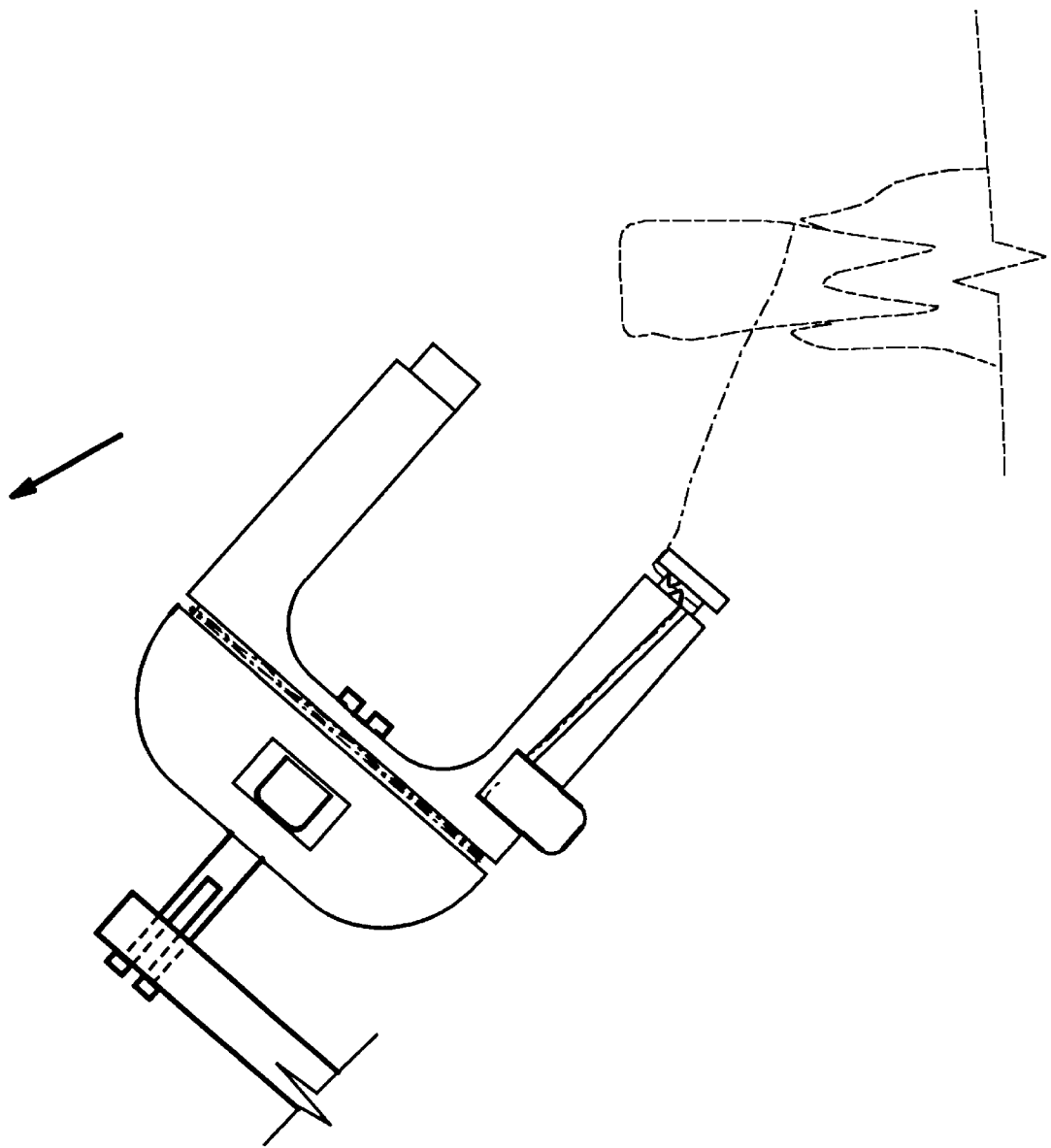
FIG. 28 is a schematic that shows that the invented device is moved upwards while the loop of the dental floss line scrubs upwards of a surface of a tooth.
Figure 29:
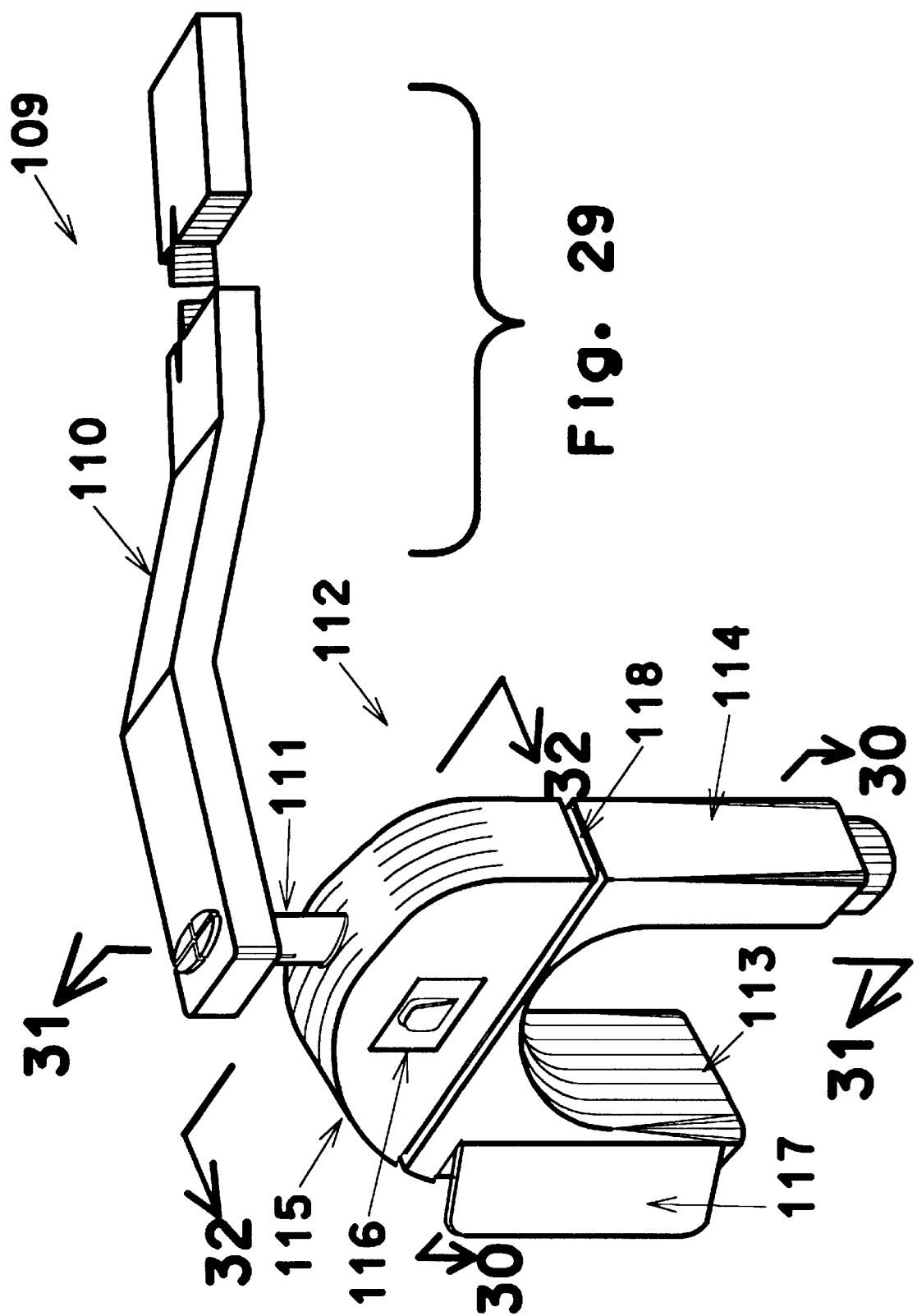
FIG. 29 is a perspective view of the six variation of the invented device.
Figure 30:
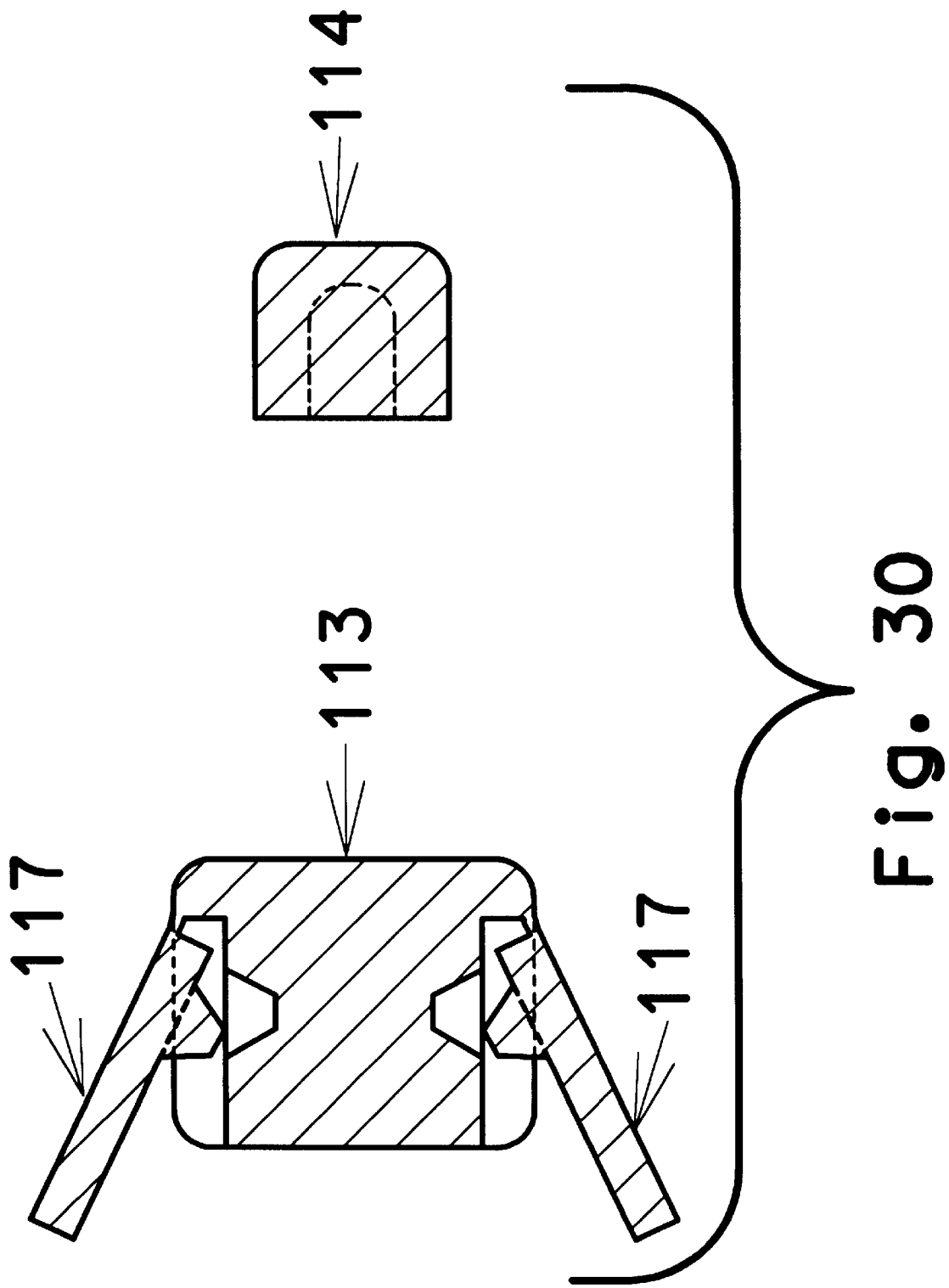
FIG. 30 is a sectional view of the device shown in FIG. 29.
Figure 31:
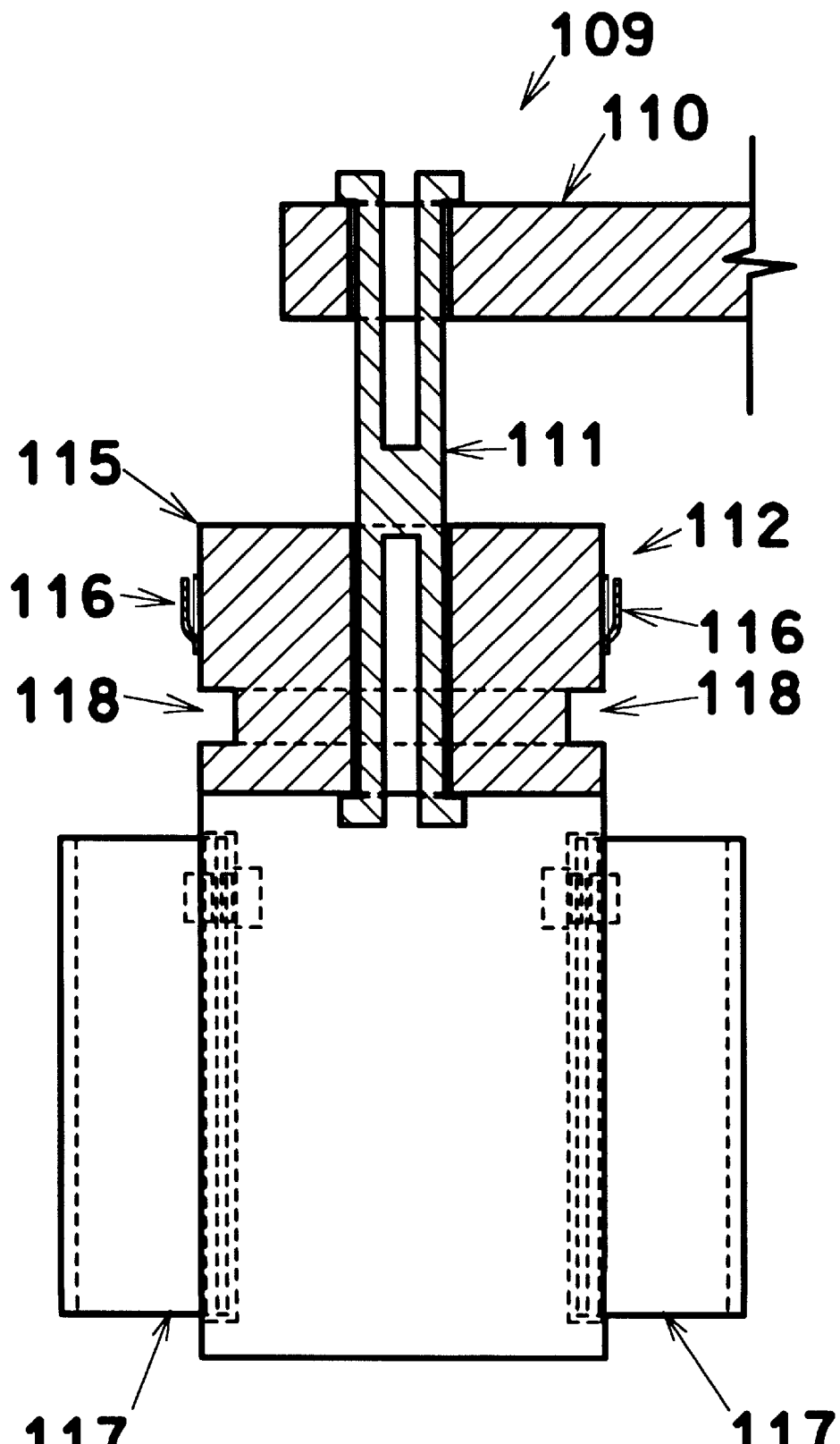
FIG. 31 is an another sectional view of the device shown in FIG. 29.
Figure 32:
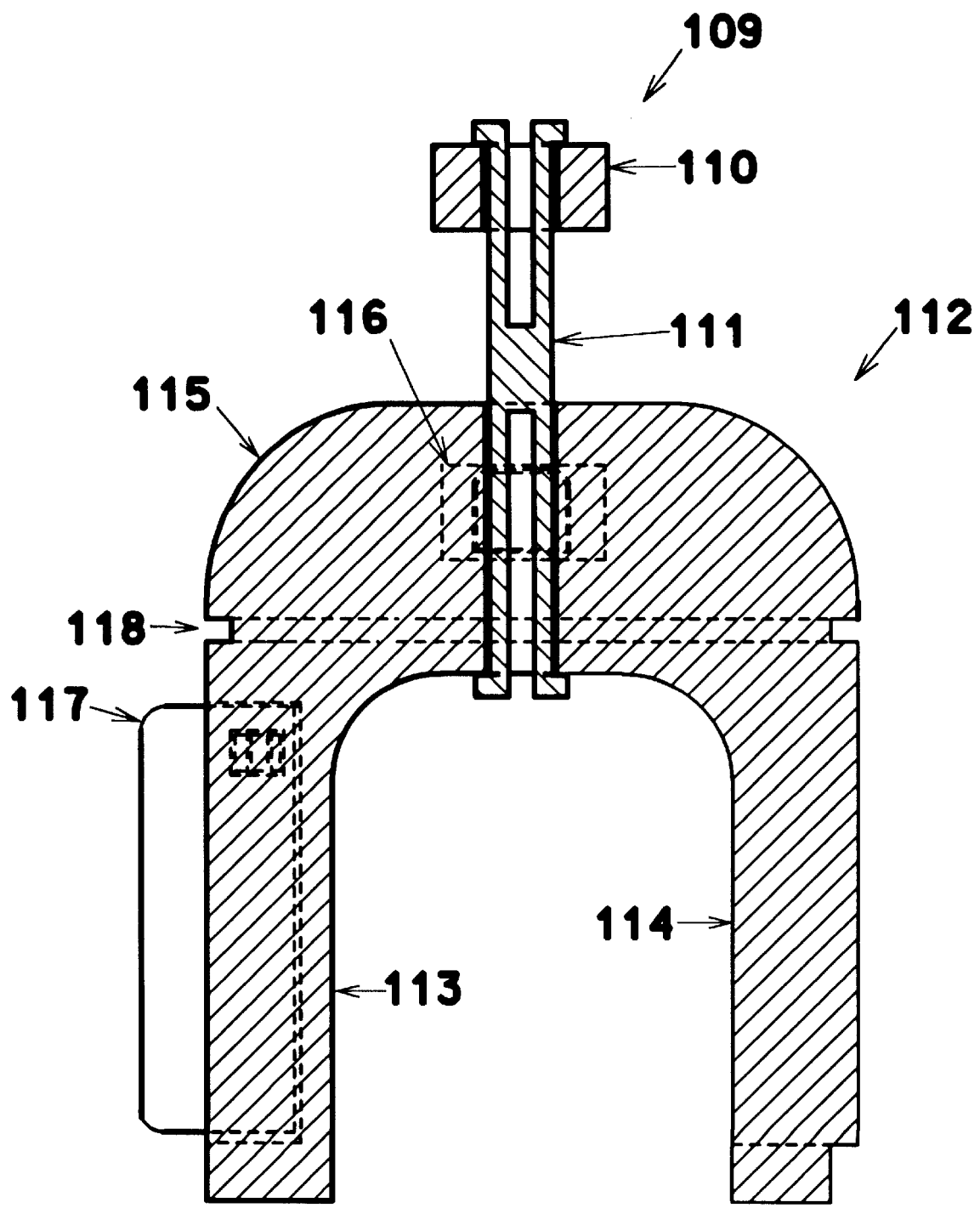
FIG. 32 is an another sectional view of the device shown in FIG. 29.

Referring to FIG. 27, the user then moves downwards the applicator head. The user can pull the applicator head slightly away from the tooth to keep adequate tautness of the dental floss when its been moved downwards. The dental floss then scrubs downwards three sides of the tooth to clean the tooth. Referring to FIG. 28, the user can move upwards the applicator head meanwhile pull slightly the applicator head away for the tooth to control the tautness of the dental floss. At this time, the dental floss will scrub to clean the tooth. With several repeated movements as described above and as shown in FIGS. 27 and 28, the teeth will be cleaned. The floss guard will prevent the dental floss being pull away from the applicator head during these movements.

When the tooth is cleaned, the user pulls the dental floss' loop out of the gaps between teeth. The user then opens the locker and un-winds the dirty dental floss. The user then un-wind a clean dental floss out of the floss holder and re-wind the clean dental floss on the extruding block and the floss groove; just as the work described previously for the preparations of using the invented devices. After the clean dental floss is winded, the user can close the locker to secure the dental floss in place. The user can trim off the dirty dental floss on the cutter; just as what people do to take a piece of dental floss from a dental floss dispenser normally.

Although FIGS. 23 through 28 illustrates the uses of the invented device for a tooth of a lower jaw, the uses of the invented device for a tooth of an upper jaw will be similar. Because the applicator head can rotate around the connector, the invented device can work equally well to clean both sides of a tooth, both the tongue-side and the cheek-side of a tooth.

The applicator heads for the second and the fourth variations of the invented devices will provide a high line and a low line for the two dental floss lines. These high and low lines of dental floss will help a user to differentiate the two lines. Therefore, these lines can be inserted into the desired gaps easily.

The foregoing is considered as illustrative only of the principles of the invention. Furthermore, since numerous modifications and changes will readily occur to those skilled in the art, it is not desired to limit the invention to the exact constructions and operations shown and described, and accordingly all suitable modifications and equivalents, may be resorted to, falling within the scope of the invention as claimed.

I claim:

1. A dental floss applicator comprising:
   a) a handle in the form of an elongated object;
   b) an applicator head in the form of a "U"-shaped object;
   c) and a connector in the form of a short rod with connections on both rod ends;
   d) one end of said connector connecting with said handle and the other end of said connector connecting with said head;

e) said U-shaped object defining at least two legs, one leg having a narrowed projection;

f) said other leg having two floss guard means thereon;

g) said applicator head having a floss locking plate which can engage with a recessed area on said applicator head.

2. The applicator of claim 1 wherein said head defines protrusions on which said first, second and third surfaces are located.

3. The applicator of claim 2 wherein said protrusions comprise legs on which said first, second and third surfaces are located, said legs spaced apart whereby said primary and secondary strands are spaced apart for reception at opposite sides of a tooth.

4. The applicator of claim 2 including notches at said protrusions, at least two of said floss engaging surfaces associated with said notches.

5. The applicator of claim 3 including a handle carrying said head and projecting away from the head, and, said legs projecting in directions away from the handle.

6. The applicator of claim 3 wherein said first and second surfaces are on a single leg spaced from the leg on which said third surface is located.

7. A dental floss applicator, comprising a) an applicator head, b) protrusions on the head defining first and second floss engaging surfaces, and a third surface spaced from the first and second surfaces to engage a primary strand of floss extending from the first surface to the third surface, and to engage a secondary strand of floss extending from the second surface to the third surface.

8. The applicator of claim 7 including a handle carrying said head and projecting away from the head.

9. The applicator of claim 7 including a floss cutting edge carried by the head.

10. The applicator of claim 7 including a floss locking structure carried by said head.

11. The applicator of claim 10 wherein said locking structure comprises a plate.

12. The applicator of claim 8 including grooving at the handle and a connection located on the handle for a floss container so that floss from the container extends in such grooving toward the head.

13. The applicator of claim 8 including a rotary connection between the handle and head.

14. The applicator of claim 7 including grooving on the head to receive and store floss in spaced relation to said surfaces.

15. The applicator of claim 14 wherein said grooving extends at least part way around the head to store floss winding about the head.

16. The applicator of claim 7 including said floss extending in a first loop from said first surface to said second surface, from said second surface to said third surface, and from said third surface to said first surface.

17. The applicator of claim 16 wherein said floss loop has a second mode position in which the loop is released and spaced from said third surface.

18. The applicator of claim 9 including two wedges on the head, at least one wedge carrying said cutting edge.

* * * * *